(12) United States Patent
Cornvik et al.

(10) Patent No.: US 11,053,302 B2
(45) Date of Patent: Jul. 6, 2021

(54) STABILIZED AND AUTONOMOUS ANTIBODY VH DOMAIN

(71) Applicant: Nanyang Technological University, Singapore (SG)

(72) Inventors: Tobias Carl Cornvik, Singapore (SG); Ignacio Jose Asial, Singapore (SG); Par Lennart Nordlund, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 15/524,731

(22) PCT Filed: Nov. 4, 2015

(86) PCT No.: PCT/SG2015/050432
§ 371 (c)(1),
(2) Date: May 5, 2017

(87) PCT Pub. No.: WO2016/072938
PCT Pub. Date: May 12, 2016

(65) Prior Publication Data
US 2017/0320934 A1    Nov. 9, 2017

(30) Foreign Application Priority Data
Nov. 5, 2014  (SG) .............................. 10201407244P

(51) Int. Cl.
| C07K 16/00 | (2006.01) |
| C07K 16/32 | (2006.01) |
| A61K 47/68 | (2017.01) |

(52) U.S. Cl.
CPC ............ C07K 16/00 (2013.01); C07K 16/005 (2013.01); C07K 16/32 (2013.01); C07K 2317/40 (2013.01); C07K 2317/569 (2013.01); C07K 2317/80 (2013.01); C07K 2317/94 (2013.01)

(58) Field of Classification Search
CPC ...... C07K 16/00; C07K 16/005; C07K 16/32; C07K 2317/40; C07K 2317/569; C07K 2317/80; C07K 2317/94; C07K 2317/567; C07K 2317/35; C07K 2317/31; A61P 43/00; A61P 35/00; A61K 47/6801; A61K 47/6879; A61K 47/6883
See application file for complete search history.

(56) References Cited

U.S. PATENT DOCUMENTS

2007/0292936 A1* 12/2007 Barthelemy ......... C07K 16/005
435/243

FOREIGN PATENT DOCUMENTS

| CN | 101312988 A | 11/2008 |
| CN | 101443043 A | 5/2009 |
| WO | 2005/052002 A2 | 6/2005 |
| WO | 2007/134050 A2 | 11/2007 |

OTHER PUBLICATIONS

Stancovski et al., PNAS 88: 8691-8695 (Year: 1991).*
Jiang et al., J. Biol. Chem 280 (6): 4656-4662 (Year: 2005).*
Paul, Fundamental Immunology, (textbook), pp. 292-295 (Year: 1993).*
Rudikoff et al (Proc. Natl. Acad. Sci. USA 79: 1979-1983. (Year: 1982).*
Asial et al., "Engineering protein thermostability using a generic activity-independent biophysical screen inside the cell," Nat. Comm. 4:2901, 2013. (8 pages).
Barthelemy et al., "Comprehensive Analysis of the Factors Contributing to the Stability and Solubility of Autonomous Human $V_H$ Domains," J. Biol. Chem.283:3639-3654, 2008.
Byrne et al., "A tale of two specificities: bispecific antibodies for therapeutic and diagnostic applications," Trends Biotechnol. 31(11):621-632, 2013.
Carter et al., "Antibody-Drug Conjugates for Cancer Therapy," Cancer J. 14(3):154-169, 2008.
Carter et al., "Humanization of an anti-p185$^{HER2}$ antibody for human cancer therapy," Proc. Natl. Acad. Sci. USA 89:4285-4289, 1992.
Chen et al., "Construction of a Large Phage-Displayed Human Antibody Domain Library with a Scaffold Based On a Newly Identified Highly Soluble, Stable Heavy Chain Variable Domain," J. Mol. Biol. 382:779-789, 2008.
Chen et al., "A large human domain antibody library combining heavy and light chain CDR3 diversity," Mol. Immun. 47:912-921, 2010.
Christ et al., "Repertoires of aggregation-resistant human antibody domains," Protein Eng. Des. Sel. 20:413-416, 2007.
Cornvik et al., "Colony filtration blot: a new screening methods for soluble protein expression in Escherichia coli," Nat. Meth.2(7):507-509, 2005.

(Continued)

Primary Examiner — Phuong Huynh
(74) Attorney, Agent, or Firm — Seed IP Law Group LLP

(57) ABSTRACT

The present invention relates to single domain antibodies comprising at least one modification relative to the 4D5 antibody scaffold or human germline VH3 domain, the modifications selected from the group consisting of H35D, A78V, S93V, S93G and W103R, with the position numbering being according to the Kabat numbering scheme. Disulfide-free variants further comprise at least one additional modification selected from the group consisting of C22S, A24I, A24L and C92T, and with the proviso that at least one of C22S and C92T is present. Further encompassed are the multi-modular antibody molecules and antibody conjugates comprising single domain antibodies, as well as methods for producing them. The invention in particular provides a library of the single domain antibodies or multi-modular antibody molecules and a method for selecting an antibody that binds an antigen.

9 Claims, 5 Drawing Sheets
Specification includes a Sequence Listing.

(56) References Cited

OTHER PUBLICATIONS

Cox et al., "A directory of human germ-line $V_x$ segments reveals a strong bias in their usage," *Eur. J. Immunol.* 24:827-836, 1994.

Dübel et al. ed., *Handbook of Therapeutic Antibodies*, 2nd ed., Wiley-Blackwell, Weinheim, Germany, 2014. (2266 pages).

Ducry et al., "Antibody—Drug Conjugates: Linking Cytotoxic Payloads to Monoclonal Antibodies," *Biconjugate Chem.* 21:5-13, 2010.

Ericsson et al., "Thermofluor-based high-throughput stability optimization of proteins for structural studies," *Anal. Biochem.* 357:289-298, 2006.

Giovannoni et al., "Isolation of anti-angiogenesis antibodies from a large combinatorial repertoire by colony filter screening," *Nucleic Acids Res.* 29(5):e27, 2001. (6 pages).

Holliger et al., "Engineered antibody fragments and the rise of single domains," *Nat. Biotech.* 23.(9):1126-1136, 2005.

Honegger et al., "The influence of the framework core residues on the biophysical properties of immunoglobulin heavy chain variable domains," *Protein Eng. Des. Sel.* 22(3):121-134, 2009.

Hong et al., "Tapping the treasure of intracellular oncotargets with immunotherapy," *FEBS Letters* 588:350-355, 2014.

Hsu et al., "Antibody Variable Domain Interface and Framework Sequence Requirements for Stability and Function by High-Throughput Experiments," *Structure* 22: 22-34, 2014.

Huang et al., "Industrial production of recombinant therapeutics in *Escherichia coli* and its recent advancements," *J. Ind. Microbiol. Biotechnol.* 39:383-399, 2012.

Jespers et al., "Aggregation-resistant domain antibodies selected on phage by heat denaturation," *Nat. Biotechnol.* 22(9):1161-1165, 2004.

Johnson et al., "Kabat Database and its applications: 30 years after the first variability plot," *Nucleic Acids Res.* 2 (1):214-218, 2000.

Knappik et al., "Fully Synthetic Human Combinatorial Antibody Libraries (HuCAL) Based on Modular Consensus Frameworks and CDRs Randomized with Trinucleotides," *J. Mol. Biol.* 296:57-86, 2000.

Kunkel, "Rapid and efficient site-specific mutagenesis without phenotypic selection," *Proc. Natl. Acad. Sci. USA* 82:488-492, 1985.

Kwong et al., "*E. coli* Expression and Purification of Fab Antibody Fragments," *Cur. Protoc. Protein Sci.* 55:6.10.1-6.10.14, 2009. (14 pages).

Liu et al., "Mapping Tumor Epitope Space by Direct Selection of Single-Chain Fv Antibody Libraries on Prostate Cancer Cells," *Cancer Research* 64:704-710, 2004.

Ma et al., "Design of Synthetic Autonomous $V_H$ Domain Libraries and Structural Analysis of a $V_H$ Domain Bound to Vascular Endothelial Growth Factor," *J. Mol. Biol.* 425:2247-2259, 2013.

Marks et al., "By-passing Immunization Human Antibodies from V-gene Libraries Displayed on Phage," *J. Mol. Biol.* 222:581-597, 1991.

Matsuda et al., "Structure an physical map of 64 variable segments in the 3' 0.8-megabase region of the human immunoglobulin heavy-chain locus," *Nat. Genet.* 3:88-94, 1993.

Meidan et al., "Emerging Technologies in Transdermal Therapeutics," *Am. J. Ther.* 11:312-316, 2004.

Miyazaki, "Creating Random Mutagenesis Libraries by Megaprimer PCR of Whole Plasmid (MEGAWHOP)," *Meth. Mol. Biol.* 231:23-28, 2003.

Mutuberria et al., "Isolation of human antibodies to tumor-associated endothelial cell markers by vitro human endothelial cell selection with phage display libraries," *J. Immunol. Meth.* 287:31-47, 2004.

Nelson, "Antibody fragments," *mAbs* 2(1):77-83, 2010.

Patton et al., "The Lungs as a Portal of Entry for Systemic Drug Delivery," *Proc. Am. Thorac. Soc.* 1:338-344, 2004.

Rubinstein et al., "Use of phage display and high-density screening for the isolation of an antibody against the 51-kDa subunit of complex I," *Anal. Biochem.* 314:294-300, 2003.

Seo et al., "Engineering antibody fragments to fold in the absence of disulfide bonds," *Protein Science* 18:259-267, 2008.

Tomlinson et al., "The Repertoire of human Germline $V_H$ Sequences Reveals about Fifty Groups of $V_H$ Segments with Different Hypervariable Loops," *J. Mol. Biol.* 227:776-798, 1992.

Venturi et al., "High Level Production of Functional Antibody Fab Fragments in an Oxidizing Bacterial Cytoplasm," *J. Mol.Biol.* 315:1-8, 2002.

Walsh, "Biopharmaceutical benchmarks of 2010," *Nat. Biotech.* 28(9):917-924, 2010.

Williams et al., "Cloning and sequencing of human immunoglobulin Vλ gene segments," *Eur. J. Immunol.* 23:1456-1461, 1993.

Winter et al., "Making Antibodies by Phage Display Technology," *Annu. Rev. Immunol.* 12:433-455, 1994.

Zolot et al., "Antibody-drug conjugates," *Nat. Rev.* 12:259-260, 2013.

Strohl et al., "Therapeutic antibody engineering—Current and future advances driving the strongest growth area in the pharmaceutical industry," *Woodhead Publishing Series in Biomedicine: Number 11*, (34 pages) (Jan. 2012).

* cited by examiner

Figure 1

A
```
1                                        20
E V Q L V E S G G G L V Q P G G S L R L 21                                       40
S C A A S G F N I K D T Y I H W V R Q A
            CDR-H1            D 41                52 a 53              59
P G K G L E W V A R I Y P T N G Y T R Y
                        CDR-H2

60                                       79
A D S V K G R F T I S A D T S K N T A Y
                                     V 80    82 a b c 83                        96
L Q M N S L R A E D T A V Y Y C S R W G
                                 V
                                 G
97    100 a b c 101                     113
G D G F Y A M D Y W G Q G T L V T V S S
  CDR-H3          R
```

B
```
1                                        20
E V Q L V E S G G G L V Q P G G S L R L 21                                       40
S C A S G F N I K D T Y I H W V R Q A
  S A              CDR-H1     D 41                52 a 53              59
P G K G L E W V A R I Y P T N G Y T R Y
                        CDR-H2

60                                       79
A D S V K G R F T I S A D T S K N T A Y
                                     V 80    82 a b c 83                        96
L Q M N S L R A E D T A V Y Y C S R W G
                                C V
                                  G
97    100 a b c 101                     113
G D G F Y A M D Y W G Q G T L V T V S S
  CDR-H3          R
```

C
```
1                                        20
E V Q L V E S G G G L V Q P G G S L R L 21                                       40
S C A A S G F N I K D T Y I H W V R Q A
            CDR-H1            G    R 41                52 a 53              59
P G K G L E W V A R I Y P T N G Y T R Y
        L             CDR-H2
        E       S
60                                       79
A D S V K G R F T I S A D T S K N T A Y 80    82 a b c 83                        96
L Q M N S L R A E D T A V Y Y C S R W G
                                 A
97    100 a b c 101                     113
G D G F Y A M D Y W G Q G T L V T V S S
  CDR-H3
```

Figure 7
Control VH-EGFP
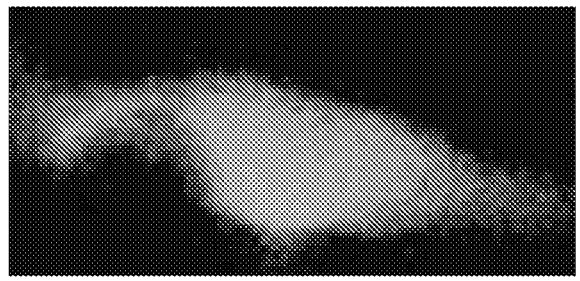
Anti-Grb2 VH-EGFP
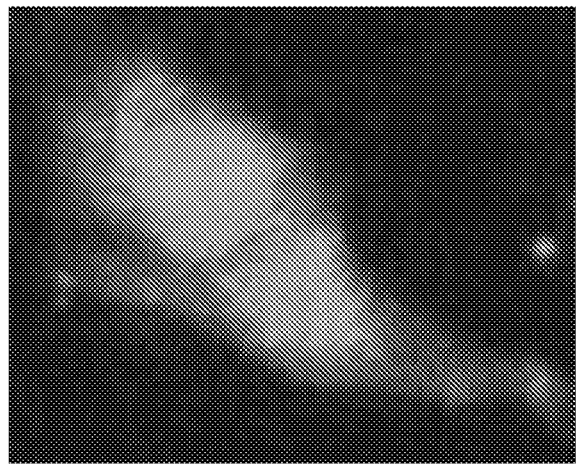

STABILIZED AND AUTONOMOUS ANTIBODY VH DOMAIN

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_519USPC_SEQUENCE_LISTING.txt. The text file is 22 KB, was created on Sep. 3, 2020, and is being submitted electronically via EFS-Web.

CROSS-REFERENCE TO RELATED APPLICATION

This application makes reference to and claims the benefit of priority of a Singapore Patent Application for "Stabilized, Autonomous, Disulfide-Free Antibody VH Domain" filed on Nov. 5, 2014, and duly assigned application number 10201407244P. The content of said application filed on Nov. 5, 2014, is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates generally to single domain antibodies. More particularly, the invention pertains to stabilized and autonomous single domain antibodies constructed on the basis of antibody VH domains.

BACKGROUND OF THE INVENTION

The pharmaceutical industry represents a market of roughly 600 billion USD, of which 100 billion USD are attributed to the ~200 biopharmaceuticals approved so far. Antibody-based products represent about 40% of the biopharmaceutical market, with some blockbusters such as monoclonal antibodies Rituxan (to treat non-Hopskin's lymphoma), Herceptin (Breast cancer) and Avastin (various cancers) representing sales for ~10 billion USD each a year (Walsh. Nat Biotechnol 2010; 28, 917-924). Their applications are continuously broadening to include a wide range of diseases, as well as many different formats to target them in the most effective ways. Full IgGs still represent the norm, but antibody fragments, antibody-drug conjugates and bi-specific antibodies are among the most promising approaches to expand the frontiers of antibody-based therapies (Byrne, et al. Trends Biotechnol 2013; 31, 621-632; Zolot, et al. Nat Rev Drug Discov 2013; 12, 259-260; Nelson. mAbs 2010; 2, 77-83). One field that remains largely unattainable is the targeting of intracellular targets by antibodies, although some successes have been reported (Hong & Zeng. FEBS Lett 2014; 588, 350-355).

VH domains are the variable domains of the human immunoglobulin heavy chains. They have potential for the generation of binders and for pharmaceutical applications. The small size of VH domains allows enhanced tumor penetration, fast clearance from the blood-stream, and makes them good candidates to target so called cryptic epitopes, i.e. narrow cavities present in viral surface antigens which are poorly accessible to intact antibodies (Barthelemy, et al. J Biol Chem 2008; 283, 3639-3654; Holliger & Hudson. Nat Biotechnol 2005; 23, 1126-1136). The development of these scaffolds has, however, been hampered by poor stability, mainly due to the loss of stabilizing interactions with the light-chain present in the intact antibody (Barthelemy, et al. J Biol Chem 2008; 283, 3639-3654; Holliger & Hudson. Nat Biotechnol 2005; 23, 1126-1136).

Previous attempts to stabilize the VH domain have yielded some success. Winter G. and colleagues developed a method to identify VH domains that were resistant to heat, and presented reversible folding in vitro (Jespers, et al. Nat Biotechnol 2004; 22, 1161-1165). Using this method they identified domain antibodies that bound β-lactamase (Christ, et al. Protein Eng Des Sel: PEDS 2007; 20, 413-416). Dimitrov D. S. and colleagues identified by serendipity an autonomous VH domain with favorable stability. Using this scaffold, they were able to generate a phage display library based on the grafting of human CDRs from donors, and identify binders against vaccinia protein BSR, IGF-1 and IGF-2 (Chen, et al. J Mol Biol 2008; 382, 779-789; Chen, et al. Mol Immunol 2010; 47, 912-921). Sidhu S. S. and co-workers attempted stabilization of 4D5 antibody (transtuzumab) VH domain, identifying mutations that allowed autonomous folding and stability. When this scaffold was used to generate a synthetic phage display library, a binder against VEGF could be identified. However, the molecule bound the target in an unconventional manner most of the binding was contributed by CDR-H3 and the former light-chain interaction surface, instead of the convectional antibody paratope composed of CDR-H1, -H2 and -H3 (Barthelemy, et al. J Biol Chem 2008; 283, 3639-3654; Ma, et al. J Mol Biol 2013; 425, 2247-2259).

Moreover, despite the progress in the generation of an autonomous, stable VH domain, there has been no success in generating a stable disulfide-free VH domain, which could be used for intracellular applications.

Therefore, there is still need in the art for stabilized antibodies that overcome the drawbacks of existing techniques.

SUMMARY OF THE INVENTION

The inventors of the present invention have found that said need can be met by the provision of the single domain antibodies of the present invention.

In a first aspect, the present invention relates to a single domain antibody, wherein the antibody is an immunoglobulin VH domain comprising at least one modification relative to a human germline VH domain or a VH domain family consensus sequence, the modifications being selected from the group consisting of H35D, A78V, S93V, S93G and W103R, with the position numbering being according to the Kabat numbering scheme.

In various embodiments, the antibody further comprises at least one additional modification relative to the human germline VH domain or the VH domain family consensus sequence, the modification being selected from the group consisting of C22S, A24I, A24L and C92T, with the position numbering being according to the Kabat numbering scheme and with the proviso that at least one of C22S and C92T is present.

In various embodiments, the antibody is based on the 4D5 antibody scaffold or a human germline VH3 domain.

In various embodiments, the antibody has the amino acid sequence EVQLVESGGGLVQPGGSLRLSCAASGF-(Xaa)$_n$-WVRQAPGKGLEWVA-(Xaa)$_p$-ADSVKGRFTI-SADTSKNT-Xaa-YLQMNSLRAEDTAVYYC-Xaa-(Xaa)$_q$-Y-Xaa-GQGTLVTVSS (SEQ ID NO:1), wherein the antibody comprises at least one modification selected from the group consisting of H35D, A78V, S93V, S93G and W103R; or has the amino acid sequence EVQLVESGG-GLVQPGGSLRLS-Xaa-A-Xaa-SGF-(Xaa)$_n$-WVRQAP-GKGLEWVA-(Xaa)$_p$-ADSVKGRFTISADTSKNT-Xaa-YLQMNSLRAEDTAVYY-Xaa-Xaa-(Xaa)$_q$-Y-Xaa-GQ-GTLVTVSS (SEQ ID NO:2), wherein the antibody comprises at least one modification selected from the group consisting of H35D, A78V, S93V, S93G and W103R and at least one modification selected from the group consisting of C22S, A24I, A24L and C92T, with the proviso that at least one of C22S and C92T is present, wherein each of n, p and q is independently 0 or an integer from 1-30, and wherein the position numbering is according to the Kabat numbering scheme. The sequences of the framework regions of SEQ ID NOS:1 and 2 as well as the corresponding SEQ NOS are listed in the table below:

| Framework region | SEQ ID NO |
|---|---|
| EVQLVESGGGLVQPGGSLRLSCAASGF | 23 |
| WVRQAPGKGLEWVA | 24 |
| ADSVKGRFTISADTSKNT-Xaa-YLQMNSLRAEDTAVYY-Xaa | 25 |
| Y-Xaa-GQGTLVTVSS | 26 |
| EVQLVESGGGLVQPGGSLRLS-Xaa-A-Xaa-SGF | 27 |
| ADSVKGRFTISADTSKNT-Xaa-YLQMNSLRAEDTAVYY-Xaa-Xaa | 28 |

In various embodiments, the antibody has one or no intramolecular disulfide bridge.

In a second aspect, the invention is directed to a multi-modular antibody molecule comprising the single domain antibody, wherein the molecule is mono-, bi- or multi-specific, and/or is mono-, bi- or multi-valent.

In a third aspect, the invention encompasses an antibody conjugate comprising the single domain antibody or the multi-modular antibody molecule, and a therapeutic agent, a detectable marker, any other payload molecule or a combination thereof.

In a fourth aspect, the invention provides a library of the single domain antibodies or the multi-modular antibody molecules of the invention, wherein each antibody comprises CDR-H1 having the amino acid sequence of Xaa-Xaa-Xaa-Xaa-T-Xaa-I-D (SEQ ID NO:3), CDR-H2 having the amino acid sequence of R-I-Xaa-P-Xaa-Xaa-G-Xaa-T-Xaa-Y (SEQ ID NO:4), and CDR-H3 having the amino acid sequence of R-(Xaa)$_n$-Xaa-Xaa-D (SEQ ID NO:5), wherein n is an integer from 6-20.

In a fifth aspect, the invention provides a method of selecting an antibody molecule that binds an antigen, said method comprising a. providing a library of the invention; b. contacting the library with the antigen so that one or more antibody molecules in the library bind to the antigen; and c. selecting the nucleic acid encoding the antibody molecule that binds to the antigen.

In a sixth aspect, the invention provides a nucleic acid molecule encoding an antibody of the invention.

In various embodiments, the nucleic acid molecule is comprised in a vector.

In a seventh aspect, the invention provides a pharmaceutical composition comprising the single domain antibody, the multi-modular antibody molecule, the antibody conjugate or the nucleic acid molecule of the invention, and a pharmaceutically acceptable carrier.

In an eighth aspect, the invention provides a method for delivering an antibody conjugate of the invention to a cell, a tumor, a tissue or an organ of a subject, comprising administering to said subject an effective amount of the antibody conjugate, wherein the antibody comprised therein is specific for an antigen of the cell, tumor, tissue or organ.

In a ninth aspect, the invention provides a method for diagnosing a disorder or disease in a subject, comprising administering to said subject an effective amount of the antibody conjugate or the pharmaceutical composition of the invention, wherein the antibody is coupled to a detectable marker, the subject being a mammal, preferably a human.

In a tenth aspect, the invention provides a method for treating a disorder or disease in a subject, comprising administering to said subject an effective amount of the antibody, the multi-modular antibody molecule, the antibody conjugate, the nucleic acid molecule, or the pharmaceutical composition of the invention, the subject being a mammal, preferably a human.

In an elevenths aspect, the invention provides a host cell comprising a nuclei acid molecule or a vector of the invention.

In a twelfth aspect, the invention provides a method of producing a single domain antibody or multi-modular antibody molecule of the invention, comprising expressing a nucleic acid encoding the single domain antibody or the multi-modular antibody molecule under conditions allowing expression of the nucleic acid.

In various embodiments, the single domain antibody or the multi-modular antibody molecule is expressed in a host cell or a cell-free system.

In a final aspect, the invention concerns the use of the single domain antibody, the multi-modular antibody molecule, the antibody conjugate, the nucleic acid molecule, or the pharmaceutical composition of the invention in a method for diagnosing or treating a disorder or disease.

BRIEF DESCRIPTION OF THE DRAWINGS

The invention will be better understood with reference to the detailed description when considered in conjunction with the non-limiting examples and the accompanying drawings.

FIG. 1 shows sequence of the improved VH-NTU(+) domain (A) (SEQ ID NO:9), the VH-NTU(−) domain (B) (SEQ ID NO:10), and comparison with Genentech's VH 1B1 (GNE; C) (SEQ ID NO:11). The original sequence of 4D5 VH domain is presented, with the preferred stabilizing mutations shown below the wild-type amino-acid, highlighted with boxes. The position numbering is according to the Kabat numbering scheme. White boxes are positions that are mutated to increase protein stability, the grey boxed are positions that are mutated to generate a disulfide-free version of the protein, and the underlined are CDR positions that can be replaced with any sequence to generate VH domain variants binding to any given target.

FIG. 7 shows fluorescent images of cells expressing control VH-EGFP (top) and anti-Grb2 VH-EGFP (bottom).

DETAILED DESCRIPTION OF THE INVENTION

Figure 2:
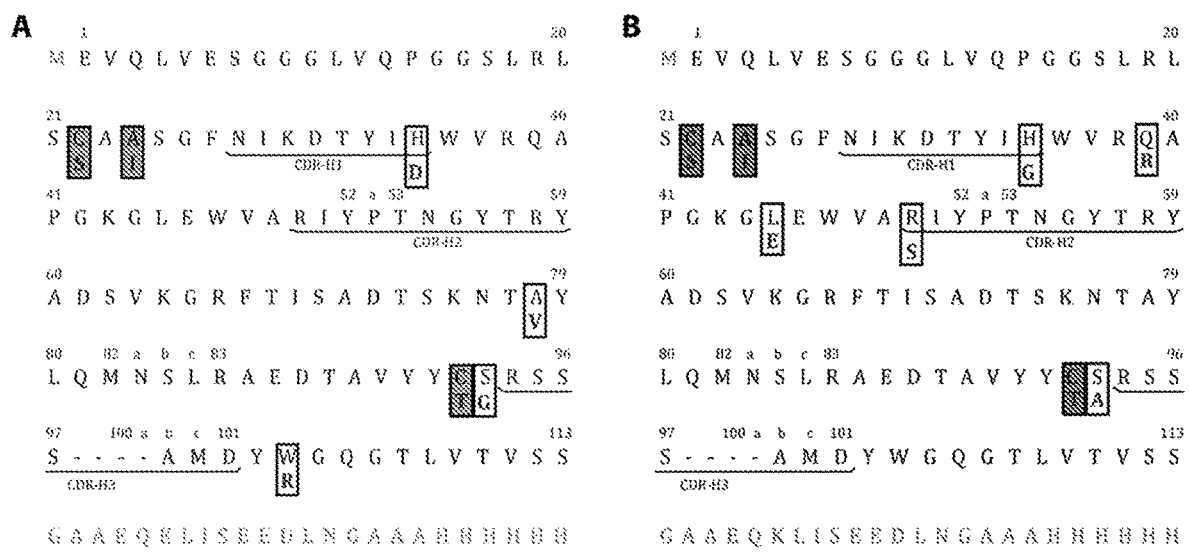
FIG. 2 shows the sequences of the scaffold VH-NTU(−) (A) (SEQ ID NO:12) and Genentech's VH scaffold 1B1 (B) (SEQ ID NO:13) compared for expression and stability. The original sequence of 4D5 VH domain is presented, with the preferred stabilizing mutations shown below the wild-type amino-acid, highlighted with boxes. The position numbering is according to the Kabat numbering scheme. CDR-H3 was replaced at positions 95-100a with the flexible sequence SSS to account for the variability expected in this CDR when generating different binders against diverse targets. White boxes are positions that are mutated to increase protein stability, the grey boxed are positions that are mutated to generate a disulfide-free version of the protein, and the underlined are CDR positions that can be replaced with any sequence to generate VH domain variants binding to any given target. The sequence in light grey is the extra sequence necessary for the expression and detection.
Figure 3:
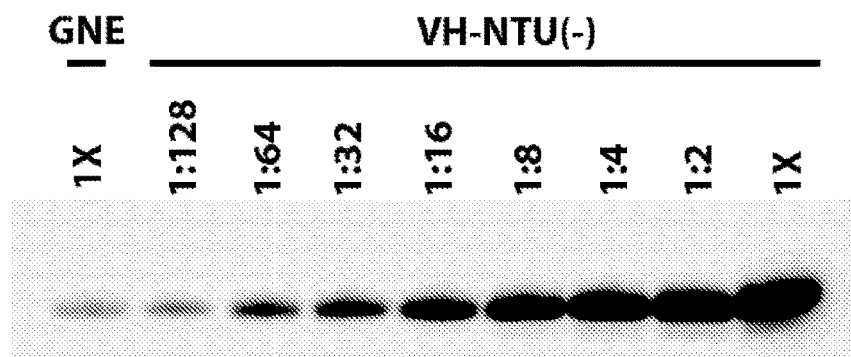
FIG. 3 shows the comparison of GNE and VH-NTU(−) soluble expression levels by western blot. An undiluted sample of GNE's soluble fraction is compared with 1:2 serial dilutions of VH-NTU(−)'s soluble fraction.

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. In case of conflict, the present document, including definitions, will control.

The object of the present invention is to provide stabilized and autonomous single domain antibodies.

To this end, the inventors of the present invention have generated a single domain antibody on the basis of an antibody VH domain by evolving protein solubility (using Colony Filtration blot, or CoFi), aggregation resistance and thermostability (by Hot Colony Filtration, or Hot-CoFi) as developed by the inventors (Asial, et al. *Nat Commun* 2013; 4, 2901; Cornvik, et al. *Nat Methods* 2005; 2, 507-509), in combination with directed evolution approaches.

In a first aspect, the present invention relates to a single domain antibody, wherein the antibody is an immunoglobulin heavy chain variable (VH) domain comprising at least one modification relative to a human germline VH domain or a VH domain family consensus sequence, the modifications being selected from the group consisting of H35D (His→Asp at position 35), A78V (Ala→Val at position 78), S93V (Ser→Val at position 93), S93G (Ser→Gly at position 93) and W103R (Trp→Arg at position 103), with the position numbering being according to the Kabat numbering scheme.

The articles "a" and "an" are used herein to refer to one or to more than one (i.e., to at least one) of the grammatical object of the article. By way of example, "an element" means at least one element and can include more than one element.

The term "antibody", as used herein, refers to a proteinaceous molecule that is capable of noncovalently, reversibly, and in a specific manner binding a corresponding antigen. Typical examples of an antibody are immunoglobulins, as well as derivatives or functional fragments thereof which still retain the binding specificity.

As well established in the art, "immunoglobulin" generally refers to a glycoprotein that includes at least two heavy (H) chains and two light (L) chains linked by disulfide bonds, or an antigen binding portion thereof. Each heavy chain has a heavy chain variable region (abbreviated herein as VH) and a heavy chain constant region (CH). The term "variable" refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "hypervariable regions" or "complementarity determining regions" (CDRs). The more conserved (i.e., non-hypervariable) portions of the variable domains are called the "framework" regions (FR). The variable domains of naturally occurring heavy and light chains each include four FR regions, largely adopting a β-sandwich configuration, connected by three hypervariable regions, which form loops connecting, and in some cases forming part of, the β-sheet structure. The hypervariable regions in each chain are held together in close proximity by the FR and, with the hypervariable regions from the other chain, contribute to the formation of the antigen-binding site. Generally, naturally occurring immunoglobulins include six CDRs: three in the VH (CDR-H1, CDR-H2, CDR-H3), and three in the VL (CDR-L1, CDR-L2, CDR-L3). An antibody VH domain comprises four framework regions, FR1, FR2, FR3 and FR4, interspersed with CDRs in the following structure: FR1-CDR1-FR2-CDR2-FR3-CDR3-FR4. In naturally occurring immunoglobulins, CDR-H3 and CDR-L3 display the most diversity of the six CDRs, and CDR-H3 in particular is believed to play a unique role in conferring fine specificity to immunoglobulins.

Researchers studying antibody structure and function have developed different schema for identifying the heavy and light chain CDRs existing within the amino acid sequence of any particular VH or VL region. Many of these schema identify CDRs according to invariant or nearly invariant patterns associated with the surrounding framework of variable heavy and light regions. The CDRs are then defined using number ranges corresponding to the position of their constituent residues within the context of the VH and VL regions. Because CDRs, in particular the third CDR, can vary in length, the schemes sometimes also use letters to define constituent residues. One of the first such schemes is known as the Kabat numbering system, which was based on aligning the then known VH and VL sequences to determine the position of variable CDR subsequences within the context of the more highly conserved framework regions. The Kabat numbering scheme is described in more detail in, for example, the *Handbook of Therapeutic Antibodies* (2007), ed. Stefan Dubel, Wiley-VCH Verlag GmbH & Co. KgaA, Weinheim, which is herein incorporated by reference.

It should be noted that the position numbering adopted in the claims and throughout the description, with the exception of the sequence listing (see below), is the numbering according to the Kabat scheme.

The present application relates to a "single domain antibody", namely an antibody fragment comprising a single protein domain that specifically binds an antigen or epitope independently of other variable regions or domains. Single domain antibodies are generally the smallest functioning binding units of antibodies and correspond to the variable regions of the heavy (VH) or light (VL) chains of antibodies. Single domain antibodies have a molecular weight of approximately 13 kDa, or less than one tenth the size of a full antibody. The antibody according to the present invention is a single domain antibody based on an VH domain whose amino acid sequence corresponds to a human germline VH domain or a VH domain family consensus sequence.

The term "germline antibody" refers to antibodies having a high amino acid sequence homology to antibodies encoded by genomic DNA sequences in the absence of somatic hypermutation. Germline antibodies generally exhibit an amino acid sequence homology in the variable region compared to the amino acid sequence encoded by the closest germline gene of at least 60%, preferably ranging from a sequence homology of 60% to 100%, or more preferably between 75% and 99%. Such antibodies have undergone minimal or no somatic hypermutation, which is characteristic of nongermline antibodies.

"Percent (%) sequence identity" with respect to amino acid sequences disclosed herein is defined as the percentage of amino acid residues in a candidate sequence that are pair-wise identical with the amino acid residues in a reference sequence, i.e. an antibody molecule of the present disclosure, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publically available computer software such as BLAST, ALIGN, or Megalign (DNASTAR) software. Those skilled in the an can determine appropriate parameters for measuring alignment, including any algorithms needed to achieve maximum alignment over the full length of the sequences being compared.

The antibody sequences are classified into distinct families according to classification methods based on sequence homology (Tomlinson, et al. *J Mol Biol* 1992; 227(3):776-798; Williams and Winter. *Eur J Immunol* 1993; 23(7):1456-1461); Cox, et al. *Eur J Immunol* 1994; 24(4):827-36). The term "VH domain family consensus sequence", as used herein, refers to the consensus sequence produced by aligning and grouping VH domain sequences that share at least 70% sequence homology. Consensus sequences of the different VH domain families are well known in the art and can be found in, for example, Kabat, E. A., et al. (1991) *Sequences of Proteins of Immunological Interest, Fifth Edition*, U.S. Department of Health and Human Services, *NIH Publication No.* 91-3242.

As an example, the 4D5 framework is an artificial framework derived from human consensus sequences, which essentially corresponds to the germline sequences, IGVH 3-66 and IGVK 1-39 (IMGT nomenclature) (Carter, et al. *Proc Natl Acad Sci USA.* 1992; 89(10):4285-9) and was originally used for the humanization of the anti-c-erbB2 (p185$^{HER2}$-ECD) mAb 4D5.

Notably, the single domain antibodies of the invention comprise at least one modification relative to a human germline VH domain or a VH domain family consensus sequence, the modifications being selected from the group consisting of H35D, A78V, S93V, S93G and W103R, with the position numbering being according to the Kabat numbering scheme. These modifications have been identified through extensive experimentation by the inventors and are introduced to increase protein stability. In the 4D5 antibody scafold, positions 78, 93 and 103 of the VH domain are within the framework region whereas position 35 falls within CDR-H1. It should be noted that although the CDR sequences can be replaced with any amino acid residues to generate VH domain variants binding to any given target, the inventors have found that the use of Asp residue at position 35 within CDR-H1 improves stability of the 4D5 scaffold. This is in line with the recent finding that a few residues in the variable domains are also conserved (Hsu, et al. *Structure.* 2014 Jan. 7; 22(1):22-34).

In various embodiments, the antibody further comprises at least one additional modification relative to the human germline VH domain or the VH domain family consensus sequence, the modification being selected from the group consisting of C22S (Cys→Ser at position 22), A24I (Ala→Ile at position 24), A24L (Ala→Leu at position 24) and C92T (Cys→Thr at position 92), with the position numbering being according to the Kabat numbering scheme and with the proviso that at least one of C22S and C92T is present. These modifications are introduced to generate a disulfide-free version of the protein.

The removal of the disulfide-bridge is advantageous by providing the possibility to express the VH domain in a soluble form recombinantly in the *E. coli* cytoplasm. Most therapeutic antibodies are currently being expressed in mammalian cell lines, in the secreted form, as they require the formation of disulfide bridges and post-translational modifications (Walsh. *Nat Biotechnol* 2010; 28, 917-924). Some antibody fragments can be produced in bacteria, but they are typically produced in an insoluble form, to be later re-folded in-vitro (Huang, et al. *J Ind Microbiol Biotechnol* 2012; 39, 383-399). This is a cumbersome process, which slows development times. Production in *E. coli* periplasm is sometimes possible, but require significant optimization of expression conditions and yields are usually low (Huang, et al. *J Ind Microbiol Biotechnol* 2012; 39, 383-399; Kwong & Rader. *Curr Protoc Protein Sci*/editorial board, John E. Coligan . . . [et al.] 2009; Chapter 6, Unit 6 10). The VH domain does not require post-translational modifications for folding, binding or stability, and therefore a disulfide-free VH could be expressed in high yields in the bacteria and in a soluble folded form. The high growth rates of bacteria compared to mammalian cells, the simplicity of the culture conditions, as well as the streamlined purification process that can be obtained by producing these molecules in the soluble form, reduce the time and cost required to produce and purify these molecules compared to other immunoglobulin formats.

In various embodiments, the antibody is based on the 4D5 antibody scaffold or a human germline VH3 domain. The VH3 germline is clearly defined in the following publications: Tomlinson et al. *JMB* 1992; 227, 776-798 and Matsuda et al. *Nat Genet* 1993; 3(1), 88-94, which are herein incorporated by reference.

It should be noted that all the modifications described above were derived in the context of the sequence of the 4D5 scaffold through extensive experimentation. However, one skilled in the art would readily appreciate that these modifications are transferable to other VH domains, particularly to those of the VH3 germline, which share significant homology with the 4D5 VH domain.

To determine whether these modifications could be transferred to another VH domain, the equivalent or corresponding counterpart residues between the two sequences are determined, typically based on the sequence or structural homology between the sequences of the two VH domains. In order to establish homology, the amino acid sequence of the first VH domain, i.e. the VH domain of the 4D5 antibody, is directly compared to the sequence of a second VH domain. After aligning the sequences, using one or more of the homology alignment programs well known in the art, such as CLUSTALW (for example using conserved residues between species), allowing for necessary insertions and deletions in order to maintain alignment (i.e. avoiding the elimination of conserved residues through arbitrary deletion and insertion), the residues equivalent or corresponding to particular amino acid residues in the primary sequence of the first VH domain are defined. Alignment of conserved residues preferably should conserve at least 20%, preferably at least 30%, preferably at least 40%, preferably at least 50%, preferably at least 60%, preferably at least 70%, preferably at least 80%, preferably at least 90%, preferably at least 95%, more preferably at least 96%, even more preferably at least 98%, even more preferably at least 99% and most preferably 100% of residues. Equivalent or corresponding counterpart residues may also be defined by determining structural homology between a first and second VH domain, that is at the level of tertiary structure for VH domains whose structures have been determined. In this case, equivalent or corresponding residues are defined as those, for which the atomic coordinates of two or more of the mainchain atoms of a particular amino acid residue of the first VH domain or precursor (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the first VH domain in which the replacement mutations are introduced, what is meant to be conveyed is that the VH domain polypeptides according to the present invention may be constructed into any second VH domain which has a significant sequence or structural homology with the first VH domain.

In various embodiments, the antibody is based on the 4D5 scaffold and has the amino acid sequence EVQLVESGG-GLVQPGGSLRLSCAASGF-(Xaa)$_n$-WVRQAPGK-GLEWVA-(Xaa)$_p$-ADSVKGRFTISADTSKNT-Xaa-YLQMNSLRAEDTAVYYC-Xaa-(Xaa)$_q$-Y-Xaa-GQGT-LVTVSS (SEQ ID NO:1), wherein the antibody comprises at least one modification selected from the group consisting of H35D, A78V, S93V, S93G and W103R, wherein each of n, p and q is independently 0 or an integer from 1-30, and wherein the position numbering is according to the Kabat numbering scheme. This antibody has an intramolecular disulfide bridge. It has high stability and low aggregation propensity, even at high concentrations.

Each of n, p and q, as defined herein, is independently 0 or an integer from 1-30, and each of the residues within the CDRs could be any amino acid residue or not present. In certain embodiments, however, an independently folding molecule, e.g. a full extra domain of 100-200 amino acids, may also be grafted to CDR-H3. It means that the CDRs can have different lengths. However, the use of the Kabat numbering scheme for the designation of the position numbers ensures that the variability of the lengths of the CDRs does not affect the numbering of the VH domain positions, especially the framework positions.

In various embodiments, the antibody is based on the 4D5 scaffold and has the amino acid sequence EVQLVESGG-GLVQPGGSLRLS-Xaa-A-Xaa-SGF-(Xaa)$_n$-WVRQAP-GKGLEWVA-(Xaa)$_p$-ADSVKGRFTISADTSKNT-Xaa-YLQMNSLRAEDTAVYY-Xaa-Xaa-(Xaa)$_q$-Y-Xaa-GQGTLVTVSS (SEQ ID NO:2), wherein the antibody comprises at least one modification selected from the group consisting of H35D, A78V, S93V, S93G and W103R and at least one modification selected from the group consisting of C22S, A24I, A24L and C92T, with the proviso that at least one of C22S and C92T is present, wherein each of n, p and q is independently 0 or an integer from 1-30, and wherein the position numbering is according to the Kabat numbering scheme. This antibody was obtained by finding mutations that could replace the cysteines involved in the intramolecular disulfide bridge of the version as described above.

It is the first described VH scaffold stable without disulfide bridges, and presents unique advantages for the targeting of intracellular molecules. Another advantage is the possibility to express this scaffold in a soluble form in the cytoplasm of bacteria, which increases yields, reduces production and purification times, and therefore reduces cost of production. One or several free cysteines could also be re-introduced on the surface, and used as anchor points for chemical crosslinking of toxic payloads, fluorophores, radioisotopes, etc.

The single domain antibodies of the invention, whether having an intramolecular disulfide bridge not, whether being based on the 4D5 scaffold or not, are designed for higher thermal stability and higher aggregation resistance.

In a second aspect, the invention is directed to a multi-modular antibody molecule comprising the single domain antibody, wherein the molecule is mono-, bi- or multi-specific, and/or is mono-, bi- or multi-valent.

The term "specificity" refers to the number of different types of epitopes to which a particular antibody can bind. If the antibody binds to only one type of epitope, the antibody is monospecific. If the antibody binds to different types of epitopes then the antibody is multispecific. For example, a bispecific multi-modular antibody allows for the recognition of two different types of epitopes. An epitope is the site on an antigen at which a given antibody binds.

The term "valency" refers to the number of antigen binding sites which an antibody has for a particular epitope. For example, a monovalent antibody has one binding site for a particular epitope.

The single domain antibody according to the invention is an autonomous binding molecule. As such, it behaves as an independent binding module. The assembly of several such antibodies, for example by genetic fusion though a peptide linker, allows the generation of multi-specific and multi-valent binding molecules. For example, the fusion of two single domain antibodies binding to different targets, through a peptide linker, generates a bi-specific molecule, the fusion of three such single domain antibodies binding to different targets generates a tri-specific molecule, and so on. By fusing identical single domain antibodies that bind to a single target, multi-valent molecules can be generated.

Other modules can also be fused to add new functions. The addition of a Fc antibody fragment, for example, would allow generating molecules with extended half-life in blood, as well as antibody effector functions (e.g. complement activation). This Fc fusion can be generated on mono-specific single domain antibody of the invention, as well as on multi-specific or multi-valent molecules generated from the fusion of several single domain antibodies. As another example, such single domain antibodies may be fused to standard IgGs to add one or several binding functions to the IgGs.

The techniques for the generation of the multi-modular molecule are within the knowledge of the person of average skill in the art.

In a third aspect, the invention encompasses an antibody conjugate comprising the single domain antibody or the multi-modular antibody molecule, and a therapeutic agent, a detectable marker, any other payload molecule, or a combination thereof.

The term "therapeutic agent", as used herein, refers to any agent that can produce a therapeutic effect in a subject; the term "detectable marker", as used herein, refers to any agent that can produce a diagnostic signal detectable by any means in a subject.

The therapeutic or detectable marker of the invention may be a protein, nucleic acid molecule, compound, small molecule, organic compound, inorganic compound, or any other molecule with the desired properties suited for the practice of the present invention.

In some embodiments, the detectable marker according to the invention may be an imaging agent. The imaging agent can be any agent known to one of skill in the art to be useful for imaging a cell, tissue or a biofilm, preferably being a medical imaging agent. Examples of medical imaging agent include, but are not limited to, magnetic resonance imaging (MRI) agents, nuclear magnetic resonance imaging (NMR) agents, positron emission tomography (PET) agents, x-ray agents, optical agents, ultrasound agents and neutron capture therapy agents.

In some embodiments, the detectable markers may be fluorescent compounds such as fluorescein, fluorescein isothiocyanate, rhodamine, 5-dimethylamine-1-napthalene-sulfonyl chloride, phycoerythrin and the like, or detectable enzymes such as alkaline phosphatase, horseradish peroxidase, glucose oxidase and the like. When the antibody is conjugated to a detectable enzyme, it is detected by adding additional reagents that the enzyme uses to produce a detectable reaction product. The antibody may also be derivatised with biotin, and detected through indirect measurement of avidin or streptavidin binding.

"Any other payload molecule", as used herein, refers to any molecule that could be directly or indirectly conjugated to an antibody of the invention. As an example, the half-life of antibody conjugates in the serum is dependent on a number of factors, but smaller antibody fragments tend to be eliminated quickly from the circulation. Accordingly, smaller constructs, for example comprising a single domain antibody and a small peptide toxin, are advantageously coupled to a polypeptide which increases serum half-life. For example, they can be coupled to HSA. Preferably, the bond to HSA is labile, for example having a defined half-life such that the construct is released from the HSA when bound to a cell, and is internalized without the HSA. A useful approach is to use a multispecific ligand construct, such that the ligand also binds HSA, maintaining it in circulation.

In some embodiments, the therapeutic or detectable marker can be directly or indirectly coupled to the antibody through covalent, electrostatic or hydrophobic interactions.

Methods for attaching a drug or other small molecule pharmaceutical to an antibody fragment are well-known. Various peptide conjugation chemistries are established in the art and include bifunctional chemical linkers such as N-succinimidyl (4-iodoacetyl)-aminobenzoate; sulfosuccinimidyl (4-iodoacelyl)-aminobenzoate; 4-succinimidyl-oxycarbonyl-[alpha]-(2-pyridyldithio) toluene; sulfosuccinimidyl-6-[[alpha]-methyl-[alpha]-(pyridyldithiol)-toluamido] hexanoate; N-succinimidyl-3-(-2-pyridyldithio)-proprionate; succinimidyl-6-[3(−(-2-pyridyldithio)-proprionamido] hexanoate; sulfosuccinimidyl-6-[3(−(-2-pyridyldithio)-propionamido]hexanoate; 3-(2-pyridyldithio)-propionyl hydrazide, Ellman's reagent, dichlorotriazinic acid, S-(2-thiopyridyl)-L-cysteine, and the like. Further bifunctional linking molecules are disclosed in U.S. Pat. Nos. 5,349,066; 5,618,528; 4,569,789; 4,952,394; and 5,137,877, as well as Corson, et al. *ACS Chem Biol* 2008; 3(11):677-692.

In some embodiments, the antibody includes cleavable linkers for the release of the payload. This configuration may be necessary for the proper functioning of certain payload molecules by escaping the inhibition such as steric hindrance imposed by the antibody molecules, when the antibody conjugate arrives at the intended site of action. In one embodiment, the linker may be an acid labile linker, such as a hydrazone linkage. Other examples of acid labile linkers include linkers formed by using cis-aconitic acid, cis-carboxylic alkatriene, polymaleic anhydride, and other acid labile linkers, such as those linkers described in U.S. Pat. Nos. 5,563,250 and 5,505,931. In one embodiment, the linker is a photo-labile linker. Examples of photo-labile linkers include those linkers described in U.S. Pat. Nos. 5,767,288 and 4,469,774, each of which is incorporated by reference in its entirety.

Polypeptide agents and polypeptide ligands, including antibodies, may be conjugated via functional or reactive groups on one (or both) polypeptide(s). These are typically formed from the side chains of particular amino acids found in the polypeptide polymer. Such reactive groups may be a cysteine side chain, a lysine side chain, or an N-terminal amine group or any other suitable reactive group. Reactive groups are capable of forming covalent bonds to the ligand to be attached. Functional groups are specific groups of atoms within either natural or non-natural amino acids which form the functional groups.

Suitable functional groups of natural amino acids are the thiol group of cysteine, the amino group of lysine, the carboxyl group of aspartate or glutamate, the guanidinium group of arginine, the phenolic group of tyrosine or the hydroxyl group of serine. Non-natural amino acids can provide a wide range of functional groups including an azide, a keto-carbonyl, an alkyne, a vinyl, or an aryl halide group. The amino and carboxyl group of the termini of the polypeptide can also serve as functional groups to form covalent bonds to a desired ligand. Alternatives to thiol-mediated conjugations can be used to attach a ligand to a polypeptide via covalent interactions. These methods may be used instead of (or in combination with) the thiol mediated methods by producing polypeptides bearing unnatural amino acids with the requisite chemical functional groups, in combination small molecules that bear the complementary functional group, or by incorporating the unnatural amino acids into a chemically or recombinantly synthesised polypeptide when the molecule is being made after the selection/isolation phase.

Techniques for conjugating antibodies to drugs and other compounds are also described in Carter & Senter. *Cancer J* 2008; 14(3):154-69 and Ducry and Stump. *Bioconjug Chem* 2010; 21(1):5-13.

In a fourth aspect, the invention provides a library of the single domain antibodies or the multi-modular antibody molecules of the present invention, wherein each antibody comprises CDR-H1 having the amino acid sequence of Xaa-Xaa-Xaa-Xaa-T-Xaa-I-D (SEQ ID NO:3), CDR-H2 having the amino acid sequence of R-I-Xaa-P-Xaa-Xaa-G-Xaa-T-Xaa-Y (SEQ ID NO:4), and CDR-H3 having the amino acid sequence of R-(Xaa)$_n$-Xaa-Xaa-D (SEQ ID NO:5), wherein n is an integer from 6-20.

The library according to the invention is designed on the basis of the single domain antibodies or the multi-modular antibody molecules of the invention in conjugation with the CDRs described herein, with each single domain antibody comprised in the library being based on the 4D5 scaffold or another VH domain and being with or without an intramolecular disulfide-bridge. As an illustrative example, Example 4 of the description describes a library of the disulfide-free single domain antibodies of the invention.

The library of the invention may be generated using various established standard methods in the art. As a preferred example, a phagemid vector may be used, containing (from 5' to 3') a periplasmic signal sequence followed by the VH domain fused to phage gene III (coding for pIII) or gene VIII (coding for pVIII). Oligonucleotides are designed containing the desired randomized CDR sequences, and incorporated into the vector by cloning using appropriately designed restriction sites, by PCR-based site-directed mutagenesis, or by Kunkel mutagenesis (Kunkel. *Proc Natl Acad Sci USA* 1985; 82(2):488-92). The DNA library is transformed into *E. coli* strains such as TG1 or XL1-blue MRF' which can be infected by a helper phage. The helper phage contains the phage genome and allows the production of the phage particles containing antibodies displayed at the surface, and packing the corresponding DNA at the core.

A variety of library formats are known and within the scope of the invention, including, but not limited to those described below in the fifth aspect of the invention.

In various embodiments, the library is a phage display library.

In a fifth aspect, the invention provides a method of selecting an antibody molecule that binds an antigen, said method comprising a. providing a library according to the fourth aspect; b. contacting the library with the antigen so that one or more antibody molecules in the library bind to the antigen; and c. selecting the nucleic acid encoding the antibody molecule that binds to the antigen.

The selecting step may comprise isolating the antibody molecule that is bound to the antigen, for example the antigen may be attached to magnetic beads or other molecules that may be recovered, thereby also recovering the antibody. The antibody molecule may be linked to its encoding nucleic acid, e.g. it may be part of a particle or replicable genetic package that contains the nucleic acid. Alternatively, the selecting step may comprise isolating bacteria that express the antibody molecule, such as in the technique of iterative colony filter screening as described below. Nucleic acid encoding the antibody molecule that binds the antigen may then be isolated, if desired.

A variety of library formats and suitable screening methods are known.

A library of antibody molecules may be a bacterial library, e.g. *E. coli*. Thus, the antibody molecules may be expressed in bacteria. This may be achieved by providing bacteria containing nucleic acid molecules encoding the antibody molecules of the library, and culturing the bacteria so that they express the antibody molecules. Nucleic acid molecules encoding the antibody molecule library are an aspect of the invention, as are bacteria containing such nucleic acid. The bacteria may conveniently be stored as glycerol stocks.

Antibody molecules may be secreted from bacteria. This allows use of the technique of iterative colony filter screening (ICFS), a two-filter sandwich assay in which hundreds of millions of antibody-expressing bacterial colonies can be screened (Giovannoni et al., *Nucleic Acids Res* 2001; 1; 29(5):E27). In ICFS, bacterial cells (typically *E. coli*) expressing the library are grown on a porous master filter in contact with a second filter coated with the antigen of interest. Antibody molecules are secreted by the bacteria and diffuse on to the second filter and thus are brought into contact with the antigen. Detection of antigen binding on the second filter allows the recovery of a number of bacterial cells, including those expressing the binding specificity of interest. In turn, those bacteria may be submitted to a second round of screening for the isolation of specific antibody molecules. Iteration of the steps refines the population of selected antibody molecules. Using this methodology, a number of specifically binding antibodies of different amino acid sequences may be recovered.

Alternatively, antibody molecules of a library may be displayed on particles or molecular complexes, rather than secreted. Suitable replicable genetic packages include yeast, bacterial or bacteriophage (e.g. T7) particles, viruses, cells or covalent, ribosomal or other in vitro display systems, each particle or molecular complex containing nucleic acid encoding the antibody VII variable domain displayed on it.

Selections using cells or protein mixtures have also been documented in the literature (Liu et al. *Cancer Res* 2004; 64, 704-710; Mutuberria et al. *J Immunol Methods* 2004; 287, 31-47; Rubinstein et al. *Anal Biochem* 2003; 314, 294-300) and these techniques may be applied in the present invention.

Phage display is an established technique for selection of antibody molecules of desired specificity, in which the library of antibody molecules is displayed on filamentous bacteriophage (Marks et al. *J Mol Biol* 1991; 222, 581-597; Winter et al. *Annu Rev Immunol* 1994; 12, 433-455). Filamentous bacteriophages are viruses that infect bacteria, and thus the phage library may be maintained in a bacterial library. The antibody molecules may be fused to an inner coat protein pIII or to the major coat protein pVIII of the phage by inserting synthetic DNA encoding the peptide into phage gene III or gene VIII respectively. Three (or possibly five) copies of pIII are thought to be located at the tip of the phage particle and about 2500 copies of pVIII are thought to be present per phage. pIII is responsible for attachment of the phage to the bacterial F-pilus and for infection, and pVIII is responsible for coating the single stranded phage DNA. The pIII protein has three domains: N1, N2 and CT. Fusions can be made to the N terminus of pIII or the N-terminal domains N1 and N2 can be removed and fusions made to the C-terminal CT domain. A gene encoding single domain antibody can be inserted into gene III, resulting in expression of the antibody molecule fused to the N terminus of pIII and incorporated into the phage, allowing the phage to bind antigen.

Nucleic acid molecules described herein may comprise a nucleotide sequence encoding an antibody molecule fused to a coat protein of filamentous bacteriophage, e.g. pIII or pVIII. Such nucleic acid molecules may be used either to express the library of antibody molecules displayed on phage that infect bacteria or to obtain soluble antibody secreted from the bacteria. By inserting an amber stop codon between the antibody molecule gene and the coat protein gene, when phage is grown in an amber suppressor strain of E. coli the amber codon is read as an amino acid and the antibody fused to the coat protein is displayed on the surface of the phage. When the phage is grown in a non-suppressor strain, the amber codon is read as a stop codon, and soluble protein is secreted from the bacteria.

Following selection of antibody molecules able to bind the antigen and displayed on bacteriophage or other library particles or molecular complexes, nucleic acid may be taken from the phage or other particle or molecular complex displaying a said selected antibody molecule. Such nucleic acid may be used in subsequent production of a single domain antibody by expression from nucleic acid with the sequence of nucleic acid taken from a bacteriophage or other particle or molecular complex displaying a said selected antibody molecule.

Thus, following selection, nucleic acid encoding the antibody molecule that binds the antigen may be expressed to produce the antibody molecule.

Once one or more antibodies have been selected from the library, the antibody molecules may be further characterised to determine their properties in a variety of assays according to the purpose for which the antibody molecule is intended. Assays may include determining affinity of the antibody molecule for binding the antigen or antigens of interest, cross-reactivity with other antigens, epitope mapping to determine which region of an antigen is hound by the antibody molecule, immunohistochemistry, and other in vitro or in vivo tests.

When necessary, the identified antibodies may be further matured or optimized towards an improved property for use in a specific application, using techniques well established in the art. The antibody molecule may also be engineered into a different format or to contain additional features.

In a sixth aspect, the invention provides a nucleic acid molecule encoding an antibody of the invention.

A nucleic acid molecule encoding one or more chains of an antibody according to the invention may be any nucleic acid in any possible configuration, such as single stranded, double stranded or a combination thereof. Nucleic acids include for instance DNA molecules, RNA molecules, analogues of the DNA or RNA generated using nucleotide analogues or using nucleic acid chemistry, locked nucleic acid molecules (LNA), and protein nucleic acids molecules (PNA). DNA or RNA may be of genomic or synthetic origin and may be single or double stranded. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues or be linked to an affinity tag or a label. The term "vector," refers to a nucleic acid molecule capable of transporting another nucleic acid to which it has been linked. In one embodiment, the vector is a "plasmid," which refers to a circular double stranded DNA loop into which additional DNA segments may be ligated. In another embodiment, the vector is a viral vector, wherein additional DNA segments may be ligated into the viral genome. The vectors disclosed herein can be capable of autonomous replication in a host cell into which they are introduced (e.g., bacterial vectors having a bacterial origin of replication and episomal mammalian vectors) or can be can be integrated into the genome of a host cell upon introduction into the host cell, and thereby are replicated along with the host genome (e.g., non-episomal mammalian vectors).

In various embodiments a nucleic acid sequence encoding a single domain antibody or multi-modular antibody molecule according to the invention is included in a vector such as a plasmid.

In a seventh aspect, the invention provides a pharmaceutical composition comprising the single domain antibody, the multi-modular antibody molecule, the antibody conjugate or the nucleic acid molecule of the invention, and a pharmaceutically acceptable carrier.

The term "pharmaceutically acceptable" is employed herein to refer to those materials, compositions, or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically-acceptable carrier" as used herein means a pharmaceutically-acceptable material, composition or vehicle, such as a liquid or solid filler, diluent, excipient, or solvent encapsulating material, involved in carrying or transporting the subject extract from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; sterile distilled water; pyrogen-free water; isotonic saline; Ringer's solution; ethyl alcohol; pH buffered solutions; polyesters, polycarbonates or polyanhydrides; and other non-toxic compatible substances employed in pharmaceutical formulations. See *Remington: The Science and Practice of Pharmacy*, 19th Ed. (Easton, Pa.: Mack Publishing Co., 1995), which discloses typical carriers and conventional methods of preparing pharmaceutical formulations.

The skilled artisan would also realize that proper formulation is dependent upon the route of administration selected for the specific application, and the proper route and mode of administering the single domain antibody, multi-modular antibody molecule, antibody conjugate or the nucleic acid molecule of the invention to a subject should be determined on a case-by-case basis.

The single domain antibody, multi-modular antibody molecule, antibody conjugate or nucleic acid molecule of the invention can be administered via any parenteral or non-parenteral (enteral) route that is therapeutically effective for proteinaceous or nucleic acid-based drugs. Parenteral application methods include, for example, intracutaneous, subcutaneous, intramuscular, intratracheal, intranasal, intravitreal or intravenous injection and infusion techniques, e.g. in the form of injection solutions, infusion solutions or tinctures, as well as aerosol installation and inhalation, e.g. in the form of aerosol mixtures, sprays or powders. An overview about pulmonary drug delivery, i.e. either via inhalation of aerosols (which can also be used in intranasal administration) or intracheal instillation is given by Patton et al. *Proc Amer Thoracic Soc* 2004; Vol. 1 pages 338-344, for example). Non-parenteral delivery modes are, for instance, orally, e.g. in the form of pills, tablets, capsules, solutions or suspensions, or rectally, e.g. in the form of suppositories. Antibody molecules of the invention can be administered systemically or topically in formulations containing conventional non-toxic pharmaceutically acceptable excipients or carriers, additives and vehicles as desired.

In one embodiment of the present invention the pharmaceutical is administered parenterally to a mammal, and in particular to humans. Corresponding administration methods include, but are not limited to, for example, intracutaneous, subcutaneous, intramuscular, intratracheal or intravenous injection and infusion techniques, e.g. in the form of injection solutions, infusion solutions or tinctures as well as aerosol installation and inhalation, e.g. in the form of aerosol mixtures, sprays or powders. A combination of intravenous and subcutaneous infusion and/or injection might be most convenient in case of compounds with a relatively short serum half life. The pharmaceutical composition may be an aqueous solution, an oil-in water emulsion or a water-in-oil emulsion.

Transdermal delivery technologies, e.g. iontophoresis, sonophoresis or microneedle-enhanced delivery, as described in Meidan V M and Michniak B B. *Am J Ther* 2004; 1 1 (4): 312-316, may also be used for transdermal delivery of a single domain antibody, multi-modular antibody molecule, antibody conjugate or nucleic acid molecule of the invention described herein. Non-parenteral delivery modes are, for instance, oral, e.g. in the form of pills, tablets, capsules, solutions or suspensions, or rectal administration, e.g. in the form of suppositories. The antibody molecules of the invention can be administered systemically or topically in formulations containing a variety of conventional non-toxic pharmaceutically acceptable excipients or carriers, additives, and vehicles.

The dosage of the single domain antibody, multi-modular antibody molecule, antibody conjugate or nucleic acid molecule of the invention applied may vary within wide limits to achieve the desired preventive effect or therapeutic response. It will, for instance, depend on the affinity of the antibody molecule for a chosen target as well as on the half-life of the complex between the antibody molecule and the ligand in vivo. Further, the optimal dosage will depend on the biodistribution of the antibody molecule or a conjugate thereof, the mode of administration, the severity of the disease/disorder being treated as well as the medical condition of the patient. For example, when used in an ointment for topical applications, a high concentration of the antibody molecule can be used. However, if wanted, the antibody molecule may also be given in a sustained release formulation, for example liposomal dispersions or hydrogel-based polymer microspheres, like PolyActive™ or OctoDEX™ (cf. Bos et al., Business Briefing: Pharmatech 2003: 1-6). Other sustained release formulations available are for example PLGA based polymers (PR pharmaceuticals), PLA-PEG based hydrogels (Medincell) and PEA based polymers (Medivas).

Accordingly, the single domain antibody, multi-modular antibody molecule, antibody conjugate or nucleic acid molecule of the present invention can be formulated into compositions using pharmaceutically acceptable ingredients as well as established methods of preparation (Gennaro, A. L. and Gennaro, A. R. (2000) Remington: The Science and Practice of Pharmacy, 20th Ed., Lippincott Williams & Wilkins, Philadelphia, Pa.). To prepare the pharmaceutical compositions, pharmaceutically inert inorganic or organic excipients can be used. To prepare e.g. pills, powders, gelatine capsules or suppositories, for example, lactose, talc, stearic acid and its salts, fats, waxes, solid or liquid polyols, natural and hardened oils can be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

The formulations can be sterilized by numerous means, including filtration through a bacteria-retaining filter, or by incorporating sterilizing agents in the form of sterile solid compositions which can be dissolved or dispersed in sterile water or other sterile medium just prior to use.

In an eighth aspect, the invention provides a method for delivering an antibody conjugate according to the third aspect to a cell, a tumor, a tissue or an organ of a subject, comprising administering to said subject an effective amount of the antibody conjugate, wherein the antibody comprised therein is specific for an antigen of the cell, tumor, tissue or organ.

By the term "effective amount" of antibody conjugate of the invention is meant a nontoxic but sufficient amount of the conjugate to provide the desired effect.

In a ninth aspect, the invention provides a method for diagnosing a disorder or disease in a subject, comprising administering to said subject an effective amount of the antibody conjugate of the invention, wherein the antibody is coupled to a detectable marker, the subject being a mammal, preferably a human.

The term "disease" or "disorder" is used interchangeably herein, and refers to any alteration in state of the body or of some of the organs, interrupting or disturbing the performance of the functions or causing symptoms such as discomfort, dysfunction, distress, or even death to the person afflicted or those in contact with a person. A disease or disorder can also relate to a distemper, ailing, ailment, malady, disorder, sickness, illness, complaint, inderdisposion or affectation.

In some embodiments, the antibodies of the invention are advantageous for molecular imaging applications due to their shorter plasma half-life relative to conventional antibodies, which achieves faster contrast-to-noise ratio needed for imaging.

In a tenth aspect, the invention provides a method for treating a disorder or disease in a subject, comprising administering to said subject an effective amount of the single domain antibody, the multi-modular antibody molecule, the antibody conjugate, the nucleic acid molecule, or the pharmaceutical composition of the invention, the subject being a mammal, preferably a human.

The terms "treating" and "treatment", as used herein, refer to reduction in severity or frequency of symptoms, elimination of symptoms or underlying cause, prevention of the occurrence of symptoms or their underlying cause, and improvement or remediation of damage. For example, treatment of a patient by administration of an anti-cancer agent of the invention encompasses chemoprevention in a patient susceptible to developing cancer (e.g., at a higher risk, as a result of genetic predisposition, environmental factors, or the like) or in cancer survivors at risk of cancer recurrence, as well as treatment of a cancer patient dual by inhibiting or causing regression of a disorder or disease.

An antibody molecule according to the invention may be directed against any desired target epitopes/antigens. Depending on the selected epitopes/antigens the antibody may be suitable in the treatment of a disorder or disease and should be determined on a case-by-case basis.

While monoclonal antibodies in the IgG format and Fabs (with current technologies) allow only the targeting of extracellular molecules for therapeutic applications, the single domain antibody in its disulfide-free version would allow targeting intracellular targets. The reducing environment inside cells leads to the dissociation of disulfide bridges and subsequent aggregation of IgGs and Fabs. Since the single domain scaffold of the invention has been evolved for stability in the absence of disulfide-bridges, its stability inside cells is not compromised. The single domain antibodies described herein can therefore be used to target intracellular molecules, or to deliver toxic payloads inside cells. The closest competitor thereof is Genentech's stable VH domain 1B1 (GNE, FIG. 1C), which still contains a disulfide bridge and is significantly less stable than the scaffold of the invention when the disulfide is removed, rendering the molecule incompatible with intracellular applications.

In addition, the small size of the antibodies of the invention presents advantages for niche therapeutic applications such as ophthalmologic treatments (e.g. wet age regaled macular degeneration, where the drug is injected into the eye and a smaller molecule would allow to pack more molecules per volume), pulmonary delivery (a smaller size could allow deeper penetration of the drug into the lungs), and the treatment of solid tumors (a smaller size allows fast tissue penetration). The smaller size can lead to reduced frequency of administration of the drug.

It is to be understood that gene therapy using a nucleic acid molecule encoding an antibody of the invention is also within the scope of the invention. By such a method, cells can be altered recombinantly to have inserted therein one or more genes of interest, such as genes coding for a single domain antibody or multi-modular antibody molecule, especially an antibody useful against a microbe, such as a virus or other pathogens, including respiratory microbes such as bacteria, fungi and parasites. Such methods are also useful in regard to other diseases via delivery of other antibodies, especially those useful in the treatment of different types of ophthalmic disease. Such cells, e.g., muscle and respiratory cells, can then be inserted into the tissues of a given organ of the recipient patient wherein the cells will express the exogenous DNA, and synthesize and secrete the antibody protein into the spaces surrounding the cells for delivery to the blood stream or local tissues, depending on where the antibody is to realize its clinical effects. Such a means of administration allows the inserted engineered cells to produce constant, possibly even inducible, levels of antibody protein without the commercial costs and problems of producing large lots of antibody that must then be stored until use. In addition, the cells can be engineered to respond to the needs of the patient in producing varying amounts of the antibody protein as required.

In some embodiments, the antibodies of the invention may be used in the secreted form, whereas the disulfide-free antibodies of the invention may also be expressed intracellularly to modulate biological processes of interest for therapeutic purposes.

In an elevenths aspect, the invention provides a host cell comprising a nuclei acid molecule or a vector of the invention.

The term "host cell" refers to a cell into which an expression vector has been introduced. Host cells include bacterial, microbial, plant or animal cells, preferably, *Escherichia coli, Bacillus subtilis; Saccharomyces cerevisiae, Pichia pastoris*, CHO (Chinese Hamster Ovary lines) or NSO cells.

In a twelfth aspect, the invention provides a method of producing a single domain antibody or multi-modular antibody molecule of the invention, comprising expressing a nucleic acid encoding the single domain antibody or the multi-modular antibody molecule under conditions allowing expression of the nucleic acid.

In various embodiments, the single domain antibody or the multi-modular antibody molecule of the invention is expressed in a host cell or a cell-free system.

An antibody molecule of the invention may be produced using any known and well-established expression system and recombinant cell culturing technology, for example, by expression in bacterial hosts (prokaryotic systems), or eukaryotic systems such as yeasts, fungi, insect cells or mammalian cells. An antibody molecule of the present invention may be produced in transgenic organisms such as a goat, a plant or a XENOMOUSE transgenic mouse, an engineered mouse strain that has large fragments of the human immunoglobulin loci and is deficient in mouse antibody production. An antibody may also be produced by chemical synthesis.

For recombinant production of an antibody molecule of the invention typically a polynucleotide encoding the antibody is isolated and inserted into a replicable vector such as a plasmid for further cloning (amplification) or expression. An illustrative example of a suitable expression system is a glutamate synthetase system (such as sold by Lonza Biologies), with the host cell being for instance CHO or NSO. A polynucleotide encoding the antibody is readily isolated and sequenced using conventional procedures. Vectors that may be used include plasmid, virus, phage, transposons, minichromsomes of which plasmids are a typical embodiment. Generally such vectors further include a signal sequence, origin of replication, one or more marker genes, an enhancer element, a promoter and transcription termination sequences operably linked to single domain antibody polynucleotide so as to facilitate expression.

When using recombinant techniques, the antibody molecule can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 1992; 10: 163-167 describe a procedure for isolating antibodies which are secreted to the periplasmic space of E coll. The polypeptide can either be directly obtained in a soluble and folded state or recovered in form of inclusion bodies, followed by renaturation in vitro. For antibodies harboring an intramolecular disulfide bridge, a further option is the use of specific host strains having an oxidizing intracellular milieu, which may thus allow the formation of disulfide bonds in the cytosol (Venturi M, Seifert C, Hunte C. *J Mol Biol* 2002; 315, 1-8).

The antibody molecule produced by the cells can be purified using any conventional purification technology, for example, hydroxylapatite chromatography, gel electrophoresis, dialysis, and affinity chromatography, with affinity chromatography being one preferred purification technique. The choice of the purification method that is used for a particular antibody molecule of the invention is within the knowledge of the person of average skill in the art.

In a final aspect, the invention concerns the use of the single domain antibody, the multi-modular antibody molecule, the antibody conjugate, the nucleic acid molecule, or the pharmaceutical composition of the invention in a method for diagnosing or treating a disorder or disease.

The present invention is further illustrated by the following examples. However, it should be understood, that the invention is not limited to the exemplified embodiments.

EXAMPLES

Methods

Library Generation for Stability Improvement.

Random mutagenesis libraries were created by error-prone PCR using Genemorph II Mutagenesis Kit (Stratagene). The cloned wild-type genes (for first library) or improved variants (for subsequent libraries) were used as templates, and the reactions were performed according to the manufacturer's protocol. The primers used annealed to sequences flanking the open reading frame (ORF) to be mutated. An average of 50 ng of insert template was used, in a 30 cycles PCR reaction with phosphorylated primers, leading to an average of ~2-3 amino-acid mutations per gene in the final plasmid library. The error-prone PCR product was gel purified (Qiagen Gel purification Kit).

The plasmid library was created by Megaprimer PCR of Whole Plasmid (MEGAWHOP) reaction (Miyazaki. *Methods Mol Biol* 2003; 231, 23), using an optimized protocol described here. Typically, 1-10 ng of plasmid containing the wild-type (WT) gene was used as template, and amplified using ~1 ng of insert per bp of insert length of purified epPCR insert as megaprimer (e.g. 500 ng for a 500 bp insert), in a PCR reaction with KOD Xtreme polymerase (Merck). The buffer composition was the standard recommended by the manufacturer, with the addition of 1 mM NAD+ and 40 U of Taq DNA ligase, and using 0.5 U of KOD Xtreme polymerase. The PCR conditions were as follows: 94° C. for 2 min, (98° C. for 10 sec, 65° C. 30 sec, 68° C. for 6 min) for 30 cycles, 4° C. on hold. After PCR, 20 U of DpnI (NEB) was added to the PCR reaction, and incubated for 3 h at 37° C.

To generate a library that would allow the identification of a disulfide-free version of VH36, first the stII signal sequence was removed by site-directed mutagenesis, generating clone VH36i. Then, a site directed mutagenesis library was generated by MEGAWHOP, in which residue positions C22, A24 and C96 were randomized. A PCR using phosphorylated forward (5'-GGCTCACTCCGTTTGTCCNNKGCANNK TCTGGCTTCAACATTAAAGAC-3') (SEQ ID NO: 7) and reverse (5'-CCTCCCCAGCGGCCMNN ATAATAGACGGCAGTG-3') (SECS ID NO: 8) primers was performed using VH36i as template, and KOD HotStart polymerase (Merck), according to the manufacturer's protocol. The PCR product was gel purified, and the MEGAWHOP reaction performed as previously, after which DpnI treatment was performed. DH10B cells were electroporated with the DpnI-treated, purified MEGAWHOP product yielding libraries of ~$10^5$ unique members.

Solubility and Stability Screening.

Rosetta2 cells were transformed with the mutagenesis libraries, and plated on 24.5 cm diameter square LB-Agar plates supplemented with 50 μg/mL kanamycin and 34 μg/mL chloramphenicol. These are considered master plates. Colonies were transferred to a Durapore 0.45 μm filter membrane (Millipore), and placed on LB-Agar plates (colonies facing up) supplemented with antibiotics and 30 μM Isopropyl β-D-1-thiogalactopyranoside (IPTG). Induction was performed overnight at room temperature (RT) for protein expression.

After protein production, the induction plates were subjected to the desired temperature (RT for solubility screen, or higher temperatures for the stability screen) for 30 min. The durapore membrane was transferred to a lysis sandwich composed of a Whatman paper, soaked in CoFi lysis buffer [20 mM Tris, pH 8.0, 100 mM NaCl, 0.2 mg/ml lysozyme, 11.2 U/mL Benzonase Endonuclease (Merck) and 1:1000 dilution of Protease Inhibitor Cocktail Set III, EDTA-Free (Merck)], and a nitrocellulose membrane (Millipore), and incubated at the screening temperature for another 30 min.

Cell lysis was further improved by three freeze-thaw cycles at −80° C. and RT, respectively (30 min each). The Durapore membrane and the Whatman paper were discarded, and the nitrocellulose membrane was incubated in blocking buffer [TBS-T buffer (20 mM Tris, pH 7.5, 500 mM NaCl, 0.05% (vol/vol) Tween 20) and 1% Bovine Serum Albumin (BSA)] for 1 h at RT.

After blocking, the nitrocellulose membrane was washed three times in TBS-T, 10 min at RT, with shaking at 70 revolutions per minute (rpm). The presence of soluble protein was detected either by incubating the membrane in TBS-T containing a 1:5,000 dilution of HisProbe-HRP (Thermo Scientific), or with a 1:10,000 dilution of protein A-HRP probe (Life Technologies) in TBS-T with 1% BSA, for 1 h at RT, with shaking at 30 rpm. Three washing steps followed, performed as previously described.

The nitrocellulose membrane was developed using Super Signal West Dura chemiluminescence kit (Thermo Scientific), using a CCD camera (Fujifilm LAS-4000).

Example 1: Generation of a Stable VH Domain by Directed Evolution and Hot-CoFi

The 4D5 VH domain was chosen as our parental scaffold for stabilization, as its parental IgG trastuzumab is an approved FDA drug with a favorable immunogenic profile and its stability has been extensively studied (Barthelemy, et al. *J Biol Chem* 2008; 283, 3639-3654). A random mutagenesis library of 4D5 VH open-reading frame (ORF) was created, and roughly 40,000 clones screened by Hot Colony Filtration (Hot-CoFi) at 80° C., leading to the identification of 22 unique positive clones.

These variants were pooled together, and used as templates for a new random mutagenesis library. The $2^{nd}$ round of screening was performed at 90° C., leading to the identification of 31 additional unique positive clones, which were further characterized. The biophysical characterization of these clones was performed by determination of the temperature of cellular aggregation ($T_{cagg}$) (Asial, et al. *Nature communications* 2013; 4, 2901), in a modified version. In this case the thermal stress was performed on full protein lysate in a PCR machine, using a gradient from 40° C. to 95° C., followed by centrifugation and filtration to remove aggregates. The soluble fraction was then dotted on a nitrocellulose membrane and developed. The $T_{cagg}$ estimated for WT is ~50° C., while the best mutant, VH36, has a $T_{cagg}$~73° C. This corresponds to a 23° C. improvement in aggregation temperature over WT.

The best two mutants identified by this work, VH33 and VH36, contain the mutations R50S, A78V, S93G, A100bP and H35D, S93G, A100bP, W103R, respectively. Interestingly, mutations in R50 and H35D are mutually exclusive in all the clones selected.

Example 2: Further Evolution for the Removal of the VH Intramolecular Disulfide Bond VH36 was chosen as the thermostable starting template for the evolution of a disulfide-free version. The signal peptide, stII, which directed VH36 towards the periplasm was removed, creating the template VH36i, which aggregated in the cytoplasm of E. coli. Three positions, C22, A24 and C92, were randomized with all 20 amino acids using NNK codons, by Kunkel mutagenesis. Roughly ~20,000 clones from this library were screened by CoFi blot, and the nitrocellulose membrane developed by protein A-HRP probe to identify soluble and folded VH36i variants. Five different variants were identified, VH36i.1 being the most stable, with a $T_m$=58° C. This clone contains mutation C22S, A24C and C96T.

In order for VH36i.1 to be useful for the generation of binders, its stability should not be dependent on its CDRs, and specially CDR-H3. Moreover, the mutation A100bP generates a downward kink in CDR-H3, which reduces CDR-H3 flexibility and therefore CDR-H3 plasticity. For this reasons, CDR-H3 was removed and replaced by the sequence SSSA from positions W95 up to P100b, creating construct VH37i. VH37i had a reduced stability, with a $T_m$=46° C. To further stabilize VH37i, a new random mutagenesis library was screened by CoFi and developed by protein A-HRP probe, with a screening step at RT and more stringent confirmation of positives at 50° C. Four stabilized clones were identified, VH37i.1 and VH37.2 being the most stables, with stabilities of $T_m$~56° C. VH37i.1 contains the core mutation A78V, while VH37i.2 contains the mutation G93V, located in close proximity with CDR-H3. Mutations from both clones were combined to generate the final clone VH38i, with a stability of $T_m$~57° C. This variant accepts several substitutions for position C24, the only cysteine in the molecule: original wild-type Ala, and mutations to Ile, Val, Tyr, Ser and Trp. C24I and C24L are the most stable variants, with $T_m$~58° C. The combination of all the knowledge acquired throughout this study led to the identification of the mutations allowing for higher stability of the VH domain in the presence or in the absence of a disulfide bridge. These preferred mutations are highlighted in FIGS. 1A and 1B, and correspond to the final scaffolds of the invention, i.e. VH-NTU(+) and VH-NTU(-), respectively.

Example 3: Comparison Between VH-NTU(-) and Genentech's VH 1B1 for Expression and Stability in the Absence of Disulfide Bridges To compare the behavior of the VH scaffold to Genentech's VH scaffold 1B1 in terms of stability in the absence of disulfide bridges, two protein constructs to be expressed in the cytoplasm of E. coli were generated (FIG. 2).

Genentech's scaffold (GNE) and the scaffold VH-NTU(-) having the amino acid sequence EVQLVESGG-GLVQPGGSLRLSSAISGFNIKDTYIDWVRQAPGK-GLEWVARIYPTNGYTR YADSVKGRFTISADTSKN-TVYLQMNSLRAEDTAVYYTGRSSSAMDYRGQGT-LVTVSS (SEQ ID NO:6) were cloned into a pET-based expression vector, and the plasmids were transformed into Rosetta2 expression strain. Expression was performed in 800 mL of TB media at 18° C. overnight. The VH-NTU(-) antibody described herein is based on the 4D5 VH domain, wherein the CDR-H3 thereof was replaced at positions 95-100a with the flexible sequence SSS to account for the variability expected in this CDR when generating different binders against diverse targets.

The cell pellet obtained for GNE and VH-NTU(-) were 18 g and 20 g, respectively. They were resuspended in 30 mL lysis buffer and lysed by sonication.

The lysate was centrifuged at 35,000 g for 15 min at 4° C., and the supernatant (soluble fraction) was retained. An aliquot from GNE's and VH-NTU(-)'s soluble fractions was loaded onto a SDS-PAGE gel. After electrophoresis, the proteins were transferred onto a nitrocellulose membrane and probed with anti-myc antibody to compare the relative levels of soluble expression for GNE and VH-NTU(-).

Figure 4:
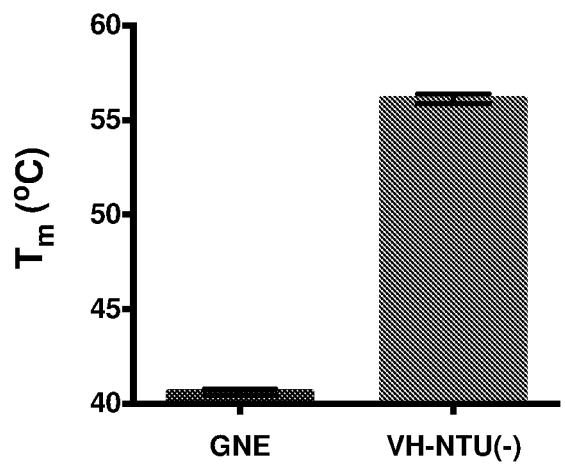
FIG. 4 shows the melting temperatures obtained for GNE and VH-NTU. $T_m$ determination was performed in triplicates. Average $T_m$ and standard deviations are plotted.

The melting temperatures ($T_m$) were determined by Differential Scanning Fluorimetry (Ericsson, et al. *Anal Biochem* 2006; 357, 289-298) (FIG. 4). GNE and VH-NTU (-) have a melting temperature $T_m$=40.6° C. and $T_m$=56.1° C., respectively. The VH-NTU(-) scaffold is therefore 16° C. more stable than Genentech's scaffold in the absence of disulfide bridges.

The data show that the scaffold VH-NTU(-) is superior to Genentech's 1B1 in the absence of disulfide bridges. The soluble expression yields in E. coli are 128× higher, and the stability is superior by 16° C. for VH-NTU(-). These advantages make the scaffold of the present invention the ideal choice for generating antibodies against intracellular targets. This has clear applications to target intracellular molecules for therapy, but also for research and imaging purposes. The higher expression yields could simplify and accelerate the production and purification process.

Example 4: Generation of Binders Against Diverse Targets Using the VH-NTU Scaffold To validate the usefulness of our scaffold, the sequence described in FIG. 2A was used as a template to generate a phage display antibody library. This library 1 contained mutations in all three CDRs H1, H2 and H3, with an amino-acid composition biased towards Tyr and Ser (FIG. 5).

Figure 6:
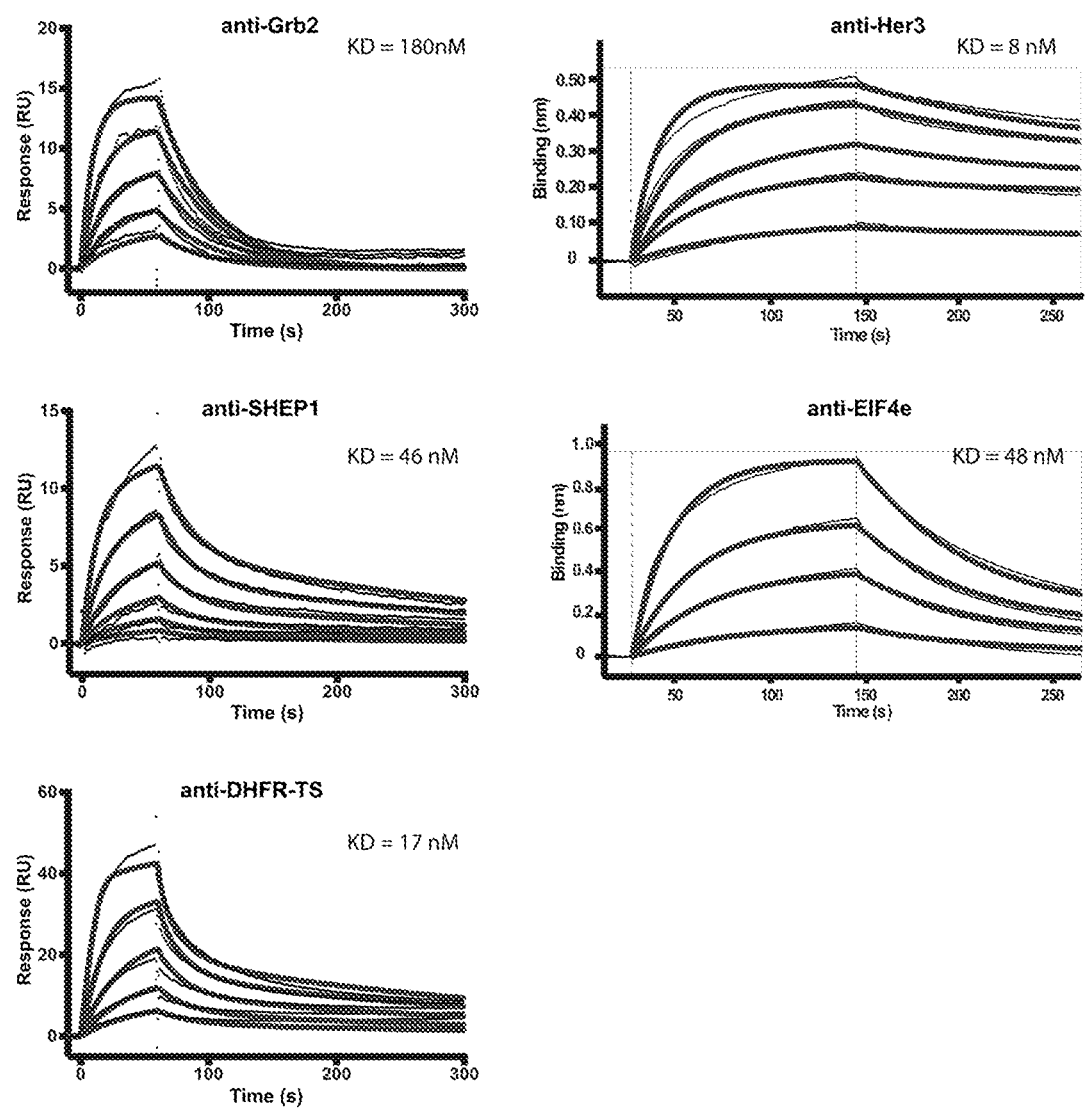
FIG. 6 shows affinity measurements of the VH-NTU(−) domains obtained against Grb2 (kinetics measured by surface plasmon resonance), SHEP1 (kinetics measured by surface plasmon resonance), DHFR-TS (kinetics measured by surface plasmon resonance), Her3 (kinetics measured by biolayer interferometry) and EIF4e (kinetics measured by biolayer interferometry). Affinities obtained (KD) are shown in the graphs. Anti-Grb2 VH: Grb2 immobilized; anti-Grb2 VH in serial 1:2 dilutions, stating at 625 nM. Anti-SHEP1 VH: SHEP1 immobilized, anti-SHEP1 VH in serial 1:2 dilutions, stating at 250 nM. Anti-DHFR-TS VH: DHFR-TS immobilized, anti-DHFR-TS VH in serial 1:2 dilutions, stating at 125 nM. Anti-Her3 VH: VH immobilized; Her3 in serial 1:2 dilutions, starting at 200 nM. Anti-EIF4e VH: EIF4e immobilized; anti-EIF4e VH in serial 1:2 dilutions, starting at 125 nM.

Using library 1, binders against three diverse targets: human growth factor receptor-bound protein 2 (Grb2), human SH2 domain-containing protein 3C (SHEP1) and *P. falciparum* bifunctional dihydrofolate reductase-thymidylate synthase (DHFR-TS) were identified. The affinities obtained range between 180 nM and 17 nM (FIG. 6).

Figure 5:
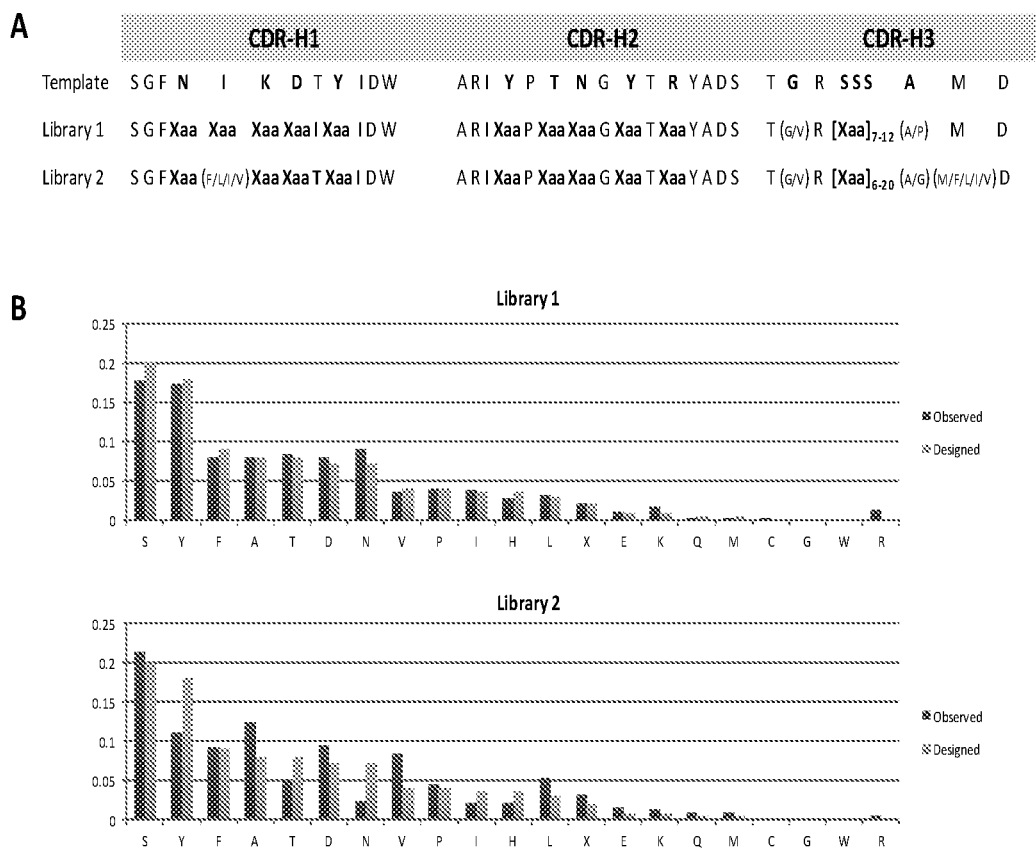
FIG. 5 shows the design for VH library 1 and VH library 2 (SEQ ID NOS:14-22) respectively. (A) Positions mutated in CDR-H1, -H2 and -H3. Note that in CDR-H3, $[Xaa]_{7-12}$ denotes the number of residues introduced with the frequency "Xaa" (from 7 to 12 residues) for library 1, while $[Xaa]_{6-20}$ denotes the number of residues introduced with the frequency "Xaa" (from 6 to 20 residues) for library 2. In these libraries, "Xaa" is coded by the degenerate codon xyz, with x=0.2G+0.2A+0.5T+0.1C, y=0.4A+0.2T+0.4C, and z=0.1G+0.9C. (B) Mutation frequencies designed and obtained for positions shown as "Xaa". "X" denotes amber codons.

A second generation library (library 2) was generated, adding improvements to the previous design: a wider range of lengths for CDR-H3; a preferred residue T32 in CDR-H1; and hydrophobic residues to replace residue I29 in the same CDR-H1 as well as residue M100c in CDR-H3 (FIG. 5). Binders against eukaryotic translation initiation factor 4E (EIF4E) and receptor tyrosine-protein kinase erbB-3 (Her3) were identified from this library. The affinities obtained using library 2 range between 48 nM and 8 nM (FIG. 6).

Example 5: Expression of Binders in Human Cancer Cells

To demonstrate that these VH domains are stable inside human cells, fusion constructs in which the VH was fused to enhanced green fluorescent protein (EGFP) were generated, giving a green fluorescence read-out when the VH was produced in a soluble form. FIG. 7 shows results of human breast cancer cells MCF-7 transfected with either anti-Grb2 VH-EGFP or control VH-EGFP. The fluorescent signal from transfected cells confirms that the VHs are able to express intracellularly and maintain stability in human cells (this was already proven for expression in E. coli cytoplasm during the comparison between the VH-NTU of the present invention and Genentech's GNE as described in Example 3).

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

What is claimed is:

1. A synthetic single domain antibody, wherein the synthetic antibody is an immunoglobulin VH domain comprising the framework sequences selected from the group consisting of
   (a) EVQLVESGGGLVQPGGSLRLSCAASGF (SEQ ID NO:23), WVRQAPGKGLEWVA (SEQ ID NO:24), ADSVKGRFTISADTSKNT-Xaa-YLQMNSLRAED-TAVYYC-Xaa (SEQ ID NO:25), and -Y-Xaa-GQGTLVTVSS (SEQ ID NO:26), wherein the synthetic antibody comprises at least one modification selected from the group consisting of A78V, S93V, S93G and W103R with the position numbering being according to the Rabat numbering scheme; and
   (b) EVQLVESGGGLVQPGGSLRLS-Xaa-A-Xaa-SGF-(SEQ ID NO:27), WVRQAPGKGLEWVA (SEQ ID NO:24), ADSVKGRFTISADTSKNT-Xaa-YLQMNSLRAEDTAVYY-Xaa-Xaa (SEQ ID NO:28), and Y-Xaa-GQGTLVTVSS (SEQ ID NO:26), wherein the synthetic antibody comprises at least one modification selected from the group consisting of A78V, S93V, S93G and W103R and at least one modification selected from the group consisting of C22S, A24I, A24L and C92T, wherein at least one of C22S and C92T is present with the position numbering being according to the Rabat numbering scheme.

2. The synthetic single domain antibody of claim 1, wherein the synthetic antibody according to (a) has an intramolecular disulfide bridge, and the synthetic antibody according to (b) has no intramolecular disulfide bridge.

3. A synthetic multi-modular antibody molecule comprising the synthetic single domain antibody of claim 1, wherein the synthetic molecule is mono-, bi- or multi-specific, and/or is mono-, bi- or multi-valent.

4. A synthetic antibody conjugate comprising a synthetic single domain antibody and/or a synthetic multi-modular antibody molecule, and one or more components selected from the group consisting of a therapeutic agent, a detectable marker, any other payload molecule, or a combination thereof; wherein the synthetic single domain antibody is an immunoglobulin VH domain comprising the framework sequences selected from the groan consisting of
   (a) EVQLVESGGGLVQPGGSLRLSCAASGF (SEQ ID NO:23), WVRQAPGKGLEWVA (SEQ ID NO:24), ADSVKGRFTISADTSKNT-Xaa-YLQMNSLRAED-TAVYYC-Xaa (SEQ ID NO:25), and Y-Xaa-GQGTLVTVSS (SEQ ID NO:26), wherein the synthetic antibody comprises at least one modification selected from the group consisting of A78V, S93V, S93G and W103R with the position numbering being according to the Rabat numbering scheme; and
   (b) EVQLVESGGGLVQPGGSLRLS-Xaa-A-Xaa-SGF (SEQ ID NO:27), WVRQAPGKGLEWVA (SEQ ID NO:24), ADSVKGRFTISADTSKNT-Xaa-YLQMNSLRAEDTAVYY-Xaa-Xaa- (SEQ ID NO:28), and Y-Xaa-GQGTLVTVSS (SEQ ID NO:26), wherein the synthetic antibody comprises at least one modification selected from the group consisting of A78V, S93V, S93G and W103R and at least one modification selected from the group consisting of C22S, A24I, A24L and C92T, wherein at least one of C22S and C92T is present with the position numbering being according to the Rabat numbering scheme;
wherein the synthetic multi-modular antibody molecule comprises the synthetic single domain antibody and is mono-, bi- or multi-specific, and/or is mono-, bi- or multi-valent.

5. A composition comprising a synthetic single domain antibody, a synthetic multi-modular antibody molecule, or a combination thereof and a pharmaceutically acceptable carrier, wherein:
(a) the synthetic single domain antibody is an immunoglobulin VH domain comprising the framework sequences selected from the group consisting of:
  i. EVQLVESGGGLVQPGGSLRLSCAASGF (SEQ ID NO:23), WVRQAPGKGLEWVA (SEQ ID NO:24), ADSVKGRFTISADTSKNT-Xaa-YLQMNSLRAEDTAVYYC-Xaa- (SEQ ID NO:25), and Y-Xaa-GQGTLVTVSS (SEQ ID NO:26), wherein the synthetic antibody comprises at least one modification selected from the group consisting of A78V, S93V, S93G and W103R with the position numbering being according to the Rabat numbering scheme; and
  ii. EVQLVESGGGLVQPGGSLRLS-Xaa-A-Xaa-SGF (SEQ ID NO:27), WVRQAPGKGLEWVA (SEQ ID NO:24), ADSVKGRFTISADTSKNT-Xaa-YLQMNSLRAEDTAVYY-Xaa-Xaa (SEQ ID NO:28), and Y-Xaa-GQGTLVTVSS (SEQ ID NO:26), wherein the synthetic antibody comprises at least one modification selected from the group consisting of A78V, S93V, S93G and W103R and at least one modification selected from the group consisting of C22S, A24I, A24L and C92T, wherein at least one of C22S and C92T is present with the position numbering being according to the Rabat numbering scheme;
(b) the synthetic multi-modular antibody molecule comprises the synthetic single domain antibody of (a), wherein the synthetic molecule is mono-, bi- or multi-specific, and/or is mono-, bi- or multi-valent.

6. A composition comprising a synthetic antibody conjugate and a pharmaceutically acceptable carrier, wherein the synthetic antibody conjugate comprises
(a) a synthetic single domain antibody that is an immunoglobulin VH domain comprising
  (i) the amino acid sequence of SEQ ID NO:9, wherein the amino acid sequence comprises at least one modification selected from the group consisting of H35D, A79V, S97V or G, and W110R;
  (ii) the amino acid sequence of SEQ ID NO: 10, wherein the amino acid sequence comprises at least one modification selected from the group consisting of C22S, A24I or L, H35D, A79V, C96T, S97V or G, and W110R; or
  (iii) the amino acid sequence of SEQ ID NO: 12, wherein the amino acid sequence comprises at least one modification selected from the group consisting of C23S, A25I, H36D, A80V, C97T, S98G, and W107R; or
(b) a synthetic multi-modular antibody molecule, which comprises the synthetic single domain antibody of (a), wherein the synthetic molecule is mono-, bi- or multi-specific, and/or is mono-, bi- or multi-valent; and
wherein the synthetic single domain antibody or the synthetic multi-modular antibody molecule is conjugated to one or more molecules selected from the group consisting of a therapeutic agent, a detectable marker, a payload molecule, and a combination thereof.

7. The synthetic antibody of claim 1, wherein the synthetic antibody comprises the amino acid sequence of SEQ ID NO:9, wherein the amino acid sequence comprises the modifications H35D, A79V, S97V or G, and W110R.

8. The synthetic antibody of claim 1, wherein the synthetic antibody comprises the amino acid sequence of SEQ ID NO: 10, wherein the amino acid sequence comprises the modifications C22S, A24I or L, H35D, A79V, C96T, S97V or G, and W110R.

9. The synthetic antibody of claim 1, wherein the synthetic antibody comprises the amino acid sequence of SEQ ID NO:6.

* * * * *

SEQUENCE LISTING

```
<160> NUMBER OF SEQ ID NOS: 28

<210> SEQ ID NO 1
<211> LENGTH: 180
<212> TYPE: PRT
<213> ORGANISM: Artificial Sequence
<220> FEATURE:
<223> OTHER INFORMATION: Artificially modified antibody
<220> FEATURE:
<221> NAME/KEY: MISC_FEATURE
<222> LOCATION: (28)..(56)
<223> OTHER INFORMATION: Xaa is any amino acid or is not present.
<220> FEATURE:
<221> NAME/KEY: MISC_FEATURE
<222> LOCATION: (57)..(57)
<223> OTHER INFORMATION: Xaa is any amino acid (preferably H) or D.
<220> FEATURE:
<221> NAME/KEY: MISC_FEATURE
<222> LOCATION: (72)..(101)
<223> OTHER INFORMATION: Xaa is any amino acid or is not present.
<220> FEATURE:
<221> NAME/KEY: MISC_FEATURE
<222> LOCATION: (120)..(120)
<223> OTHER INFORMATION: Xaa is A or V.
<220> FEATURE:
<221> NAME/KEY: MISC_FEATURE
<222> LOCATION: (138)..(138)
<223> OTHER INFORMATION: Xaa is S, V or G.
<220> FEATURE:
<221> NAME/KEY: MISC_FEATURE
<222> LOCATION: (139)..(168)
<223> OTHER INFORMATION: Xaa is any amino acid or is not present.
<220> FEATURE:
<221> NAME/KEY: MISC_FEATURE
<222> LOCATION: (170)..(170)
<223> OTHER INFORMATION: Xaa is W or R.
```

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
                35                  40                  45

Xaa Xaa Xaa Xaa Xaa Xaa Xaa Xaa Trp Val Arg Gln Ala Pro Gly
        50                  55                  60

Lys Gly Leu Glu Trp Val Ala Xaa Xaa Xaa Xaa Xaa Xaa Xaa Xaa Xaa
65              70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Ala Asp Ser Val Lys Gly Arg Phe Thr Ile Ser
            100                 105                 110

Ala Asp Thr Ser Lys Asn Thr Xaa Tyr Leu Gln Met Asn Ser Leu Arg
            115                 120                 125

Ala Glu Asp Thr Ala Val Tyr Tyr Cys Xaa Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Tyr Xaa Gly Gln Gly Thr Leu Val
                165                 170                 175

Thr Val Ser Ser
            180
```

<210> SEQ ID NO 2
<211> LENGTH: 180
<212> TYPE: PRT
<213> ORGANISM: Artificial Sequence
<220> FEATURE:
<223> OTHER INFORMATION: Artificially modified antibody
<220> FEATURE:
<221> NAME/KEY: MISC_FEATURE
<222> LOCATION: (22)..(22)
<223> OTHER INFORMATION: Xaa is C or S.
<220> FEATURE:
<221> NAME/KEY: MISC_FEATURE
<222> LOCATION: (24)..(24)
<223> OTHER INFORMATION: Xaa is A, I or L.
<220> FEATURE:
<221> NAME/KEY: MISC_FEATURE
<222> LOCATION: (28)..(56)
<223> OTHER INFORMATION: Xaa is any amino acid or is not present.
<220> FEATURE:
<221> NAME/KEY: MISC_FEATURE
<222> LOCATION: (57)..(57)
<223> OTHER INFORMATION: Xaa is any amino acid (preferably H) or is D.
<220> FEATURE:
<221> NAME/KEY: MISC_FEATURE
<222> LOCATION: (72)..(101)
<223> OTHER INFORMATION: Xaa is any amino acid or is not present.
<220> FEATURE:
<221> NAME/KEY: MISC_FEATURE
<222> LOCATION: (120)..(120)
<223> OTHER INFORMATION: Xaa is A or V.
<220> FEATURE:
<221> NAME/KEY: MISC_FEATURE
<222> LOCATION: (137)..(137)
<223> OTHER INFORMATION: Xaa is C or T.
<220> FEATURE:
<221> NAME/KEY: MISC_FEATURE
<222> LOCATION: (138)..(138)
<223> OTHER INFORMATION: Xaa is S, V or G.
<220> FEATURE:
<221> NAME/KEY: MISC_FEATURE

```
<222> LOCATION: (139)..(168)
<223> OTHER INFORMATION: Xaa is any amino acid or is not present.
<220> FEATURE:
<221> NAME/KEY: MISC_FEATURE
<222> LOCATION: (170)..(170)
<223> OTHER INFORMATION: Xaa is W or R.

<400> SEQUENCE: 2

Glu Val Gln Leu Val Glu Ser Gly Gly Gly Leu Val Gln Pro Gly Gly
1               5                   10                  15

Ser Leu Arg Leu Ser Xaa Ala Xaa Ser Gly Phe Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Trp Val Arg Gln Ala Pro Gly
    50                  55                  60

Lys Gly Leu Glu Trp Val Ala Xaa Xaa Xaa Xaa Xaa Xaa Xaa Xaa
65              70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Ala Asp Ser Val Lys Gly Arg Phe Thr Ile Ser
        100                 105                 110

Ala Asp Thr Ser Lys Asn Thr Xaa Tyr Leu Gln Met Asn Ser Leu Arg
        115                 120                 125

Ala Glu Asp Thr Ala Val Tyr Tyr Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Tyr Xaa Gly Gln Gly Thr Leu Val
                165                 170                 175

Thr Val Ser Ser
            180

<210> SEQ ID NO 3
<211> LENGTH: 8
<212> TYPE: PRT
<213> ORGANISM: Artificial Sequence
<220> FEATURE:
<223> OTHER INFORMATION: Artificially modified antibody
<220> FEATURE:
<221> NAME/KEY: misc_feature
<222> LOCATION: (1)..(1)
<223> OTHER INFORMATION: Xaa is any amino acid or is not present.
<220> FEATURE:
<221> NAME/KEY: MISC_FEATURE
<222> LOCATION: (2)..(2)
<223> OTHER INFORMATION: Xaa is F, L, I or V.
<220> FEATURE:
<221> NAME/KEY: MISC_FEATURE
<222> LOCATION: (3)..(4)
<223> OTHER INFORMATION: Xaa is any amino acid or is not present.
<220> FEATURE:
<221> NAME/KEY: MISC_FEATURE
<222> LOCATION: (6)..(6)
<223> OTHER INFORMATION: Xaa is any amino acid or is not present.

<400> SEQUENCE: 3

Xaa Xaa Xaa Xaa Thr Xaa Ile Asp
1               5

<210> SEQ ID NO 4
<211> LENGTH: 11
<212> TYPE: PRT
<213> ORGANISM: Artificial Sequence
```

```
<220> FEATURE:
<223> OTHER INFORMATION: Artificially modified antibody
<220> FEATURE:
<221> NAME/KEY: MISC_FEATURE
<222> LOCATION: (3)..(3)
<223> OTHER INFORMATION: Xaa is any amino acid or is not present.
<220> FEATURE:
<221> NAME/KEY: MISC_FEATURE
<222> LOCATION: (5)..(6)
<223> OTHER INFORMATION: Xaa is any amino acid or is not present.
<220> FEATURE:
<221> NAME/KEY: MISC_FEATURE
<222> LOCATION: (8)..(8)
<223> OTHER INFORMATION: Xaa is any amino acid or is not present.
<220> FEATURE:
<221> NAME/KEY: MISC_FEATURE
<222> LOCATION: (10)..(10)
<223> OTHER INFORMATION: Xaa is any amino acid or is not present.

<400> SEQUENCE: 4

Arg Ile Xaa Pro Xaa Xaa Gly Xaa Thr Xaa Tyr
1               5                   10

<210> SEQ ID NO 5
<211> LENGTH: 24
<212> TYPE: PRT
<213> ORGANISM: Artificial Sequence
<220> FEATURE:
<223> OTHER INFORMATION: Artificially modified antibody
<220> FEATURE:
<221> NAME/KEY: MISC_FEATURE
<222> LOCATION: (2)..(7)
<223> OTHER INFORMATION: Xaa is any amino acid.
<220> FEATURE:
<221> NAME/KEY: MISC_FEATURE
<222> LOCATION: (8)..(21)
<223> OTHER INFORMATION: Xaa is any amino acid or is not present.
<220> FEATURE:
<221> NAME/KEY: MISC_FEATURE
<222> LOCATION: (22)..(22)
<223> OTHER INFORMATION: Xaa is A or G.
<220> FEATURE:
<221> NAME/KEY: MISC_FEATURE
<222> LOCATION: (23)..(23)
<223> OTHER INFORMATION: Xaa is M, F, L, I or V.

<400> SEQUENCE: 5

Arg Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Asp
            20

<210> SEQ ID NO 6
<211> LENGTH: 116
<212> TYPE: PRT
<213> ORGANISM: Artificial Sequence
<220> FEATURE:
<223> OTHER INFORMATION: Artificially modified antibody

<400> SEQUENCE: 6

Glu Val Gln Leu Val Glu Ser Gly Gly Gly Leu Val Gln Pro Gly Gly
1               5                   10                  15

Ser Leu Arg Leu Ser Ser Ala Ile Ser Gly Phe Asn Ile Lys Asp Thr
            20                  25                  30

Tyr Ile Asp Trp Val Arg Gln Ala Pro Gly Lys Gly Leu Glu Trp Val
        35                  40                  45

Ala Arg Ile Tyr Pro Thr Asn Gly Tyr Thr Tyr Ala Asp Ser Val
    50                  55                  60

Lys Gly Arg Phe Thr Ile Ser Ala Asp Thr Ser Lys Asn Thr Val Tyr
```

```
            65                  70                  75                  80
Leu Gln Met Asn Ser Leu Arg Ala Glu Asp Thr Ala Val Tyr Tyr Thr
                    85                  90                  95

Gly Arg Ser Ser Ser Ala Met Asp Tyr Arg Gly Gln Gly Thr Leu Val
                100                 105                 110

Thr Val Ser Ser
        115
```

```
<210> SEQ ID NO 7
<211> LENGTH: 48
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (19)...(20)
<223> OTHER INFORMATION: N = A or G or C or T
<220> FEATURE:
<221> NAME/KEY: misc_feature
<222> LOCATION: 21
<223> OTHER INFORMATION: N = G or T
<220> FEATURE:
<221> NAME/KEY: misc_feature
<222> LOCATION: (25)...(26)
<223> OTHER INFORMATION: N = A,G,C or T
<220> FEATURE:
<221> NAME/KEY: misc_feature
<222> LOCATION: 27
<223> OTHER INFORMATION: n = G or T

<400> SEQUENCE: 7
ggctcactcc gtttgtccnn ngcannntct ggcttcaaca ttaaagac                    48

<210> SEQ ID NO 8
<211> LENGTH: 33
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: 15
<223> OTHER INFORMATION: n = A or C
<220> FEATURE:
<221> NAME/KEY: misc_feature
<222> LOCATION: (16)...(17)
<223> OTHER INFORMATION: n = A, C, G or T

<400> SEQUENCE: 8
cctccccagc ggccnnnata atagacggca gtg                                   33

<210> SEQ ID NO 9
<211> LENGTH: 120
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: 35
<223> OTHER INFORMATION: Xaa = H or D
<220> FEATURE:
<221> NAME/KEY: VARIANT
<222> LOCATION: 79
<223> OTHER INFORMATION: Xaa = A or V
<220> FEATURE:
<221> NAME/KEY: VARIANT
<222> LOCATION: 97
<223> OTHER INFORMATION: Xaa = S or V or G
<220> FEATURE:
```

```
<221> NAME/KEY: VARIANT
<222> LOCATION: 110
<223> OTHER INFORMATION: Xaa = W or R

<400> SEQUENCE: 9
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |

| | | | | | | | | | | | |
|---|---|---|---|---|---|---|---|---|---|---|---|
| Ser | Leu | Arg | Leu | Ser | Cys | Ala | Ala | Ser | Gly | Phe | Asn | Ile | Lys | Asp | Thr |
| | | 20 | | | | | 25 | | | | | 30 | | | |

Tyr Ile Xaa Trp Val Arg Gln Ala Pro Gly Lys Gly Leu Glu Trp Val
          35                  40                  45

Ala Arg Ile Tyr Pro Thr Asn Gly Tyr Thr Arg Tyr Ala Asp Ser Val
 50                      55                      60

Lys Gly Arg Phe Thr Ile Ser Ala Asp Thr Ser Lys Asn Thr Xaa Tyr
 65                  70                  75                  80

Leu Gln Met Asn Ser Leu Arg Ala Glu Asp Thr Ala Val Tyr Tyr Cys
              85                  90                  95

Xaa Arg Trp Gly Gly Asp Gly Phe Tyr Ala Met Asp Tyr Xaa Gly Gln
              100                 105                 110

Gly Thr Leu Val Thr Val Ser Ser
          115                 120

```
<210> SEQ ID NO 10
<211> LENGTH: 120
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: 22
<223> OTHER INFORMATION: Xaa = C or S
<220> FEATURE:
<221> NAME/KEY: VARIANT
<222> LOCATION: 24
<223> OTHER INFORMATION: Xaa = A or I or L
<220> FEATURE:
<221> NAME/KEY: VARIANT
<222> LOCATION: 35
<223> OTHER INFORMATION: Xaa = H or D
<220> FEATURE:
<221> NAME/KEY: VARIANT
<222> LOCATION: 79
<223> OTHER INFORMATION: Xaa = A or V
<220> FEATURE:
<221> NAME/KEY: VARIANT
<222> LOCATION: 96
<223> OTHER INFORMATION: Xaa = C or T
<220> FEATURE:
<221> NAME/KEY: VARIANT
<222> LOCATION: 97
<223> OTHER INFORMATION: Xaa = S or V or G
<220> FEATURE:
<221> NAME/KEY: VARIANT
<222> LOCATION: 110
<223> OTHER INFORMATION: Xaa = W or R

<400> SEQUENCE: 10
```

Glu Val Gln Leu Val Glu Ser Gly Gly Gly Leu Val Gln Pro Gly Gly
 1               5                  10                  15

Ser Leu Arg Leu Ser Xaa Ala Xaa Ser Gly Phe Asn Ile Lys Asp Thr
             20                  25                  30

Tyr Ile Xaa Trp Val Arg Gln Ala Pro Gly Lys Gly Leu Glu Trp Val
          35                  40                  45

Ala Arg Ile Tyr Pro Thr Asn Gly Tyr Thr Arg Tyr Ala Asp Ser Val
 50                      55                      60

```
Lys Gly Arg Phe Thr Ile Ser Ala Asp Thr Ser Lys Asn Thr Xaa Tyr
 65                  70                  75                  80

Leu Gln Met Asn Ser Leu Arg Ala Glu Asp Thr Ala Val Tyr Tyr Xaa
                 85                  90                  95

Xaa Arg Trp Gly Gly Asp Gly Phe Tyr Ala Met Asp Tyr Xaa Gly Gln
            100                 105                 110

Gly Thr Leu Val Thr Val Ser Ser
        115                 120

<210> SEQ ID NO 11
<211> LENGTH: 120
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: 35
<223> OTHER INFORMATION: Xaa = H or G
<220> FEATURE:
<221> NAME/KEY: VARIANT
<222> LOCATION: 39
<223> OTHER INFORMATION: Xaa = Q or R
<220> FEATURE:
<221> NAME/KEY: VARIANT
<222> LOCATION: 45
<223> OTHER INFORMATION: Xaa = L or E
<220> FEATURE:
<221> NAME/KEY: VARIANT
<222> LOCATION: 50
<223> OTHER INFORMATION: Xaa = R or S
<220> FEATURE:
<221> NAME/KEY: VARIANT
<222> LOCATION: 97
<223> OTHER INFORMATION: Xaa =  S or A

<400> SEQUENCE: 11

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
                20                  25                  30

Tyr Ile Xaa Trp Val Arg Xaa Ala Pro Gly Lys Gly Xaa Glu Trp Val
            35                  40                  45

Ala Xaa Ile Tyr Pro Thr Asn Gly Tyr Thr Arg Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Xaa Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 12
<211> LENGTH: 141
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: 23
<223> OTHER INFORMATION: Xaa = C or S
<220> FEATURE:
```

```
<221> NAME/KEY: VARIANT
<222> LOCATION: 25
<223> OTHER INFORMATION: Xaa = A or I
<220> FEATURE:
<221> NAME/KEY: VARIANT
<222> LOCATION: 36
<223> OTHER INFORMATION: Xaa = H or D
<220> FEATURE:
<221> NAME/KEY: VARIANT
<222> LOCATION: 80
<223> OTHER INFORMATION: Xaa = A or V
<220> FEATURE:
<221> NAME/KEY: VARIANT
<222> LOCATION: 97
<223> OTHER INFORMATION: Xaa = C or T
<220> FEATURE:
<221> NAME/KEY: VARIANT
<222> LOCATION: 98
<223> OTHER INFORMATION: Xaa = S or G
<220> FEATURE:
<221> NAME/KEY: VARIANT
<222> LOCATION: 107
<223> OTHER INFORMATION: Xaa = W or R

<400> SEQUENCE: 12

Met Glu Val Gln Leu Val Glu Ser Gly Gly Gly Leu Val Gln Pro Gly
1               5                   10                  15

Gly Ser Leu Arg Leu Ser Xaa Ala Xaa Ser Gly Phe Asn Ile Lys Asp
            20                  25                  30

Thr Tyr Ile Xaa Trp Val Arg Gln Ala Pro Gly Lys Gly Leu Glu Trp
        35                  40                  45

Val Ala Arg Ile Tyr Pro Thr Asn Gly Tyr Thr Arg Tyr Ala Asp Ser
50                  55                  60

Val Lys Gly Arg Phe Thr Ile Ser Ala Asp Thr Ser Lys Asn Thr Xaa
65                  70                  75                  80

Tyr Leu Gln Met Asn Ser Leu Arg Ala Glu Asp Thr Ala Val Tyr Tyr
                85                  90                  95

Xaa Xaa Arg Ser Ser Ser Ala Met Asp Tyr Xaa Gly Gln Gly Thr Leu
            100                 105                 110

Val Thr Val Ser Ser Gly Ala Ala Glu Gln Lys Leu Ile Ser Glu Glu
        115                 120                 125

Asp Leu Asn Gly Ala Ala Ala His His His His His
        130                 135                 140

<210> SEQ ID NO 13
<211> LENGTH: 141
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: 23
<223> OTHER INFORMATION: Xaa = C or S
<220> FEATURE:
<221> NAME/KEY: VARIANT
<222> LOCATION: 25
<223> OTHER INFORMATION: Xaa = A or I
<220> FEATURE:
<221> NAME/KEY: VARIANT
<222> LOCATION: 36
<223> OTHER INFORMATION: Xaa = H or G
<220> FEATURE:
<221> NAME/KEY: VARIANT
<222> LOCATION: 40
<223> OTHER INFORMATION: Xaa = Q or R
<220> FEATURE:
<221> NAME/KEY: VARIANT
<222> LOCATION: 46
```

```
<223> OTHER INFORMATION: Xaa = L or E
<220> FEATURE:
<221> NAME/KEY: VARIANT
<222> LOCATION: 51
<223> OTHER INFORMATION: Xaa = R or S
<220> FEATURE:
<221> NAME/KEY: VARIANT
<222> LOCATION: 97
<223> OTHER INFORMATION: Xaa =  is C or T
<220> FEATURE:
<221> NAME/KEY: VARIANT
<222> LOCATION: 98
<223> OTHER INFORMATION: Xaa = S or A

<400> SEQUENCE: 13

Met Glu Val Gln Leu Val Glu Ser Gly Gly Gly Leu Val Gln Pro Gly
1               5                   10                  15

Gly Ser Leu Arg Leu Ser Xaa Ala Xaa Ser Gly Phe Asn Ile Lys Asp
            20                  25                  30

Thr Tyr Ile Xaa Trp Val Arg Xaa Ala Pro Gly Lys Gly Xaa Glu Trp
        35                  40                  45

Val Ala Xaa Ile Tyr Pro Thr Asn Gly Tyr Thr Arg Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Xaa Xaa Arg Ser Ser Ser Ala Met Asp Tyr Trp Gly Gln Gly Thr Leu
            100                 105                 110

Val Thr Val Ser Ser Gly Ala Ala Glu Gln Lys Leu Ile Ser Glu Glu
        115                 120                 125

Asp Leu Asn Gly Ala Ala Ala His His His His His His
    130                 135                 140

<210> SEQ ID NO 14
<211> LENGTH: 12
<212> TYPE: PRT
<213> ORGANISM: Artificial Sequence
<220> FEATURE:
<223> OTHER INFORMATION: Synthetic sequence

<400> SEQUENCE: 14

Ser Gly Phe Asn Ile Lys Asp Thr Tyr Ile Asp Trp
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (1)...(12)
<223> OTHER INFORMATION: Xaa = any amino acid

<400> SEQUENCE: 15

Ser Gly Phe Xaa Xaa Xaa Xaa Ile Xaa Ile Asp Trp
1               5                   10

<210> SEQ ID NO 16
<211> LENGTH: 11
<212> TYPE: PRT
<213> ORGANISM: Artificial Sequence
<220> FEATURE:
```

```
<223> OTHER INFORMATION: Synthetic sequence
<220> FEATURE:
<221> NAME/KEY: VARIANT
<222> LOCATION: 4
<223> OTHER INFORMATION: Xaa = any amino acid
<220> FEATURE:
<221> NAME/KEY: VARIANT
<222> LOCATION: 5
<223> OTHER INFORMATION: Xaa = F, I, L or V
<220> FEATURE:
<221> NAME/KEY: VARIANT
<222> LOCATION: (6)...(11)
<223> OTHER INFORMATION: Xaa = any amino acid

<400> SEQUENCE: 16

Ser Gly Phe Xaa Xaa Xaa Thr Xaa Ile Asp Trp
1               5                   10

<210> SEQ ID NO 17
<211> LENGTH: 15
<212> TYPE: PRT
<213> ORGANISM: Artificial Sequence
<220> FEATURE:
<223> OTHER INFORMATION: Synthetic sequence

<400> SEQUENCE: 17

Ala Arg Ile Tyr Pro Thr Asn Gly Tyr Thr Arg Tyr Ala Asp Ser
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (1)...(15)
<223> OTHER INFORMATION: Xaa = any amino acid

<400> SEQUENCE: 18

Ala Arg Ile Xaa Pro Xaa Xaa Gly Xaa Thr Xaa Tyr Ala Asp Ser
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (1)...(15)
<223> OTHER INFORMATION: Xaa = any amino acid

<400> SEQUENCE: 19

Ala Arg Ile Xaa Pro Xaa Xaa Gly Xaa Thr Xaa Tyr Ala Asp Ser
1               5                   10                  15

<210> SEQ ID NO 20
<211> LENGTH: 9
<212> TYPE: PRT
<213> ORGANISM: Artificial Sequence
<220> FEATURE:
<223> OTHER INFORMATION: Synthetic sequence

<400> SEQUENCE: 20

Thr Gly Arg Ser Ser Ser Ala Met Asp
1               5
```

```
<210> SEQ ID NO 21
<211> LENGTH: 18
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: 2
<223> OTHER INFORMATION: Xaa = G or V
<220> FEATURE:
<221> NAME/KEY: VARIANT
<222> LOCATION: (11)...(15)
<223> OTHER INFORMATION: any one or all of amino acids 11-15 can either
      be present or absent.
<220> FEATURE:
<221> NAME/KEY: VARIANT
<222> LOCATION: (4)...(15)
<223> OTHER INFORMATION: Xaa = any amino acid
<220> FEATURE:
<221> NAME/KEY: VARIANT
<222> LOCATION: 16
<223> OTHER INFORMATION: Xaa = A or P

<400> SEQUENCE: 21

Thr Xaa Arg Xaa Xaa Xaa Xaa Xaa Xaa Xaa Xaa Xaa Xaa Xaa Xaa
1               5                   10                  15

Met Asp

<210> SEQ ID NO 22
<211> LENGTH: 26
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: 2
<223> OTHER INFORMATION: Xaa = G or V
<220> FEATURE:
<221> NAME/KEY: VARIANT
<222> LOCATION: (10)...(23)
<223> OTHER INFORMATION: any one or all of amino acids 10-23 can either
      be present or absent.
<220> FEATURE:
<221> NAME/KEY: VARIANT
<222> LOCATION: (4)...(23)
<223> OTHER INFORMATION: Xaa = any amino acid
<220> FEATURE:
<221> NAME/KEY: VARIANT
<222> LOCATION: 24
<223> OTHER INFORMATION: Xaa = A or G
<220> FEATURE:
<221> NAME/KEY: VARIANT
<222> LOCATION: 25
<223> OTHER INFORMATION: Xaa = M, F, L, I, or V

<400> SEQUENCE: 22

Thr Xaa Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Asp
            20                  25

<210> SEQ ID NO 23
<211> LENGTH: 27
<212> TYPE: PRT
<213> ORGANISM: Artificial
<220> FEATURE:
<223> OTHER INFORMATION: Antibody sequence motif

<400> SEQUENCE: 23
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe
            20                  25
```

<210> SEQ ID NO 24
<211> LENGTH: 14
<212> TYPE: PRT
<213> ORGANISM: Artificial
<220> FEATURE:
<223> OTHER INFORMATION: Antibody sequence motif

<400> SEQUENCE: 24

```
Trp Val Arg Gln Ala Pro Gly Lys Gly Leu Glu Trp Val Ala
1               5                   10
```

<210> SEQ ID NO 25
<211> LENGTH: 37
<212> TYPE: PRT
<213> ORGANISM: Artificial
<220> FEATURE:
<223> OTHER INFORMATION: Antibody sequence motif
<220> FEATURE:
<221> NAME/KEY: MISC_FEATURE
<222> LOCATION: (19)..(19)
<223> OTHER INFORMATION: Xaa is A or V
<220> FEATURE:
<221> NAME/KEY: MISC_FEATURE
<222> LOCATION: (37)..(37)
<223> OTHER INFORMATION: Xaa is S, V or G

<400> SEQUENCE: 25

```
Ala Asp Ser Val Lys Gly Arg Phe Thr Ile Ser Ala Asp Thr Ser Lys
1               5                   10                  15

Asn Thr Xaa Tyr Leu Gln Met Asn Ser Leu Arg Ala Glu Asp Thr Ala
            20                  25                  30

Val Tyr Tyr Cys Xaa
                35
```

<210> SEQ ID NO 26
<211> LENGTH: 12
<212> TYPE: PRT
<213> ORGANISM: Artificial
<220> FEATURE:
<223> OTHER INFORMATION: Antibody sequence motif
<220> FEATURE:
<221> NAME/KEY: MISC_FEATURE
<222> LOCATION: (2)..(2)
<223> OTHER INFORMATION: Xaa is W or R

<400> SEQUENCE: 26

```
Tyr Xaa Gly Gln Gly Thr Leu Val Thr Val Ser Ser
1               5                   10
```

<210> SEQ ID NO 27
<211> LENGTH: 27
<212> TYPE: PRT
<213> ORGANISM: Artificial
<220> FEATURE:
<223> OTHER INFORMATION: Antibody sequence motif
<220> FEATURE:
<221> NAME/KEY: MISC_FEATURE
<222> LOCATION: (22)..(22)
<223> OTHER INFORMATION: Xaa is C or S
<220> FEATURE:
<221> NAME/KEY: MISC_FEATURE
<222> LOCATION: (24)..(24)
<223> OTHER INFORMATION: Xaa is A, I or L

```
<400> SEQUENCE: 27

Glu Val Gln Leu Val Glu Ser Gly Gly Gly Leu Val Gln Pro Gly Gly
1               5                   10                  15

Ser Leu Arg Leu Ser Xaa Ala Xaa Ser Gly Phe
            20              25

<210> SEQ ID NO 28
<211> LENGTH: 37
<212> TYPE: PRT
<213> ORGANISM: Artificial
<220> FEATURE:
<223> OTHER INFORMATION: Antibody sequence motif
<220> FEATURE:
<221> NAME/KEY: MISC_FEATURE
<222> LOCATION: (19)..(19)
<223> OTHER INFORMATION: Xaa is A or V
<220> FEATURE:
<221> NAME/KEY: MISC_FEATURE
<222> LOCATION: (36)..(36)
<223> OTHER INFORMATION: Xaa is C or T
<220> FEATURE:
<221> NAME/KEY: MISC_FEATURE
<222> LOCATION: (37)..(37)
<223> OTHER INFORMATION: Xaa is S, V or G

<400> SEQUENCE: 28

Ala Asp Ser Val Lys Gly Arg Phe Thr Ile Ser Ala Asp Thr Ser Lys
1               5                   10                  15

Asn Thr Xaa Tyr Leu Gln Met Asn Ser Leu Arg Ala Glu Asp Thr Ala
            20                  25                  30

Val Tyr Tyr Xaa Xaa
            35
```

UNITED STATES PATENT AND TRADEMARK OFFICE
CERTIFICATE OF CORRECTION

PATENT NO. : 11,053,302 B2  
APPLICATION NO. : 15/524731  
DATED : July 6, 2021  
INVENTOR(S) : Tobias Carl Cornvik et al.

Page 1 of 1

It is certified that error appears in the above-identified patent and that said Letters Patent is hereby corrected as shown below:

In the Claims

Column 49, Claim 1, Line 50:
"being according to the Rabat numbering scheme; and" should read: --being according to the Kabat numbering scheme; and--.

Column 49, Claim 1, Line 62:
"being according to the Rabat numbering scheme." should read: --being according to the Kabat numbering scheme.--.

Column 50, Claim 4, Line 47:
"framework sequences selected from the groan consisting of" should read: --framework sequences selected from the group consisting of--.

Column 50, Claim 4, Line 56:
"being according to the Rabat numbering scheme; and" should read: --being according to the Kabat numbering scheme; and--.

Column 51, Claim 4, Line 2:
"being according to the Rabat numbering scheme;" should read: --being according to the Kabat numbering scheme;--.

Column 51, Claim 5, Line 22:
"being according to the Rabat numbering scheme; and" should read: --being according to the Kabat numbering scheme; and--.

Column 51, Claim 5, Line 35:
"position numbering being according to the Rabat numbering scheme;" should read: --position numbering being according to the Kabat numbering scheme;--.

Signed and Sealed this  
Twenty-first Day of March, 2023

Katherine Kelly Vidal  
*Director of the United States Patent and Trademark Office*